(12) United States Patent
Taniguchi et al.

(10) Patent No.: US 7,662,769 B2
(45) Date of Patent: Feb. 16, 2010

(54) GLYCOSYLTRANSFERASE GNT-V HAVING NEOVASCULARIZATION ACTION

(75) Inventors: Naoyuki Taniguchi, Toyonaka (JP); Eiji Miyoshi, Toyonaka (JP); Takashi Saito, Wako (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 10/500,841

(22) PCT Filed: Dec. 27, 2002

(86) PCT No.: PCT/JP02/13879
§ 371 (c)(1),
(2), (4) Date: Feb. 15, 2005

(87) PCT Pub. No.: WO03/060131
PCT Pub. Date: Jul. 24, 2003

(65) Prior Publication Data
US 2005/0148516 A1  Jul. 7, 2005

(30) Foreign Application Priority Data
Jan. 9, 2002  (JP) .............................. 2002-002056

(51) Int. Cl.
- A61K 38/00 (2006.01)
- C12N 9/10 (2006.01)
- C12N 15/00 (2006.01)
- C12Q 1/68 (2006.01)
- A61K 38/04 (2006.01)
- C12P 21/08 (2006.01)
- C07H 21/04 (2006.01)

(52) U.S. Cl. .............................. 514/2; 514/17; 435/193; 435/320.1; 435/69.1; 435/6; 530/327; 530/330; 530/388.26; 536/23.2

(58) Field of Classification Search ................. 435/193, 435/15; 514/17; 530/328
See application file for complete search history.

(56) References Cited

U.S. PATENT DOCUMENTS
6,191,113 B1 * 2/2001 Nakahara et al. .............. 514/13
6,932,973 B2   8/2005 Barritault et al.

FOREIGN PATENT DOCUMENTS
| EP | 585109 | 3/1994 |
| JP | 9-84582 | 3/1997 |
| JP | 10-137000 | 5/1998 |
| WO | WO-01/27136 A2 | 4/2001 |
| WO | WO-02/34767 | * 5/2002 |
| WO | WO-02/34767 A1 | 5/2002 |

OTHER PUBLICATIONS

Tischer et al. The human gene for vascular endothelial growth factor. Multiple protein forms are encoded through alternative exon splicing, J Biol Chem. Jun. 25, 1991;266(18):11947-54.*
Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a malonyl decarboxylase by replacemnt of the active-site cysteine with glutamine. Biochemistry, 1999, vol. 38: 11643-11650.*
Murata K. et al., "Expression of N-acetylglucosaminyltransferase V in colorectal cancer correlates with metastasis and poor prognosis," Clin. Cancer Res., 2000, vol. 6, No. 5, pp. 1772-1777.
Sasai K. et al., "The critical role of the stem region as a finctional domain responsible for the oligomerization and golgi localization of N-acetylglucosaminyltransferase V," J. Biol. Chem., 2001, vol. 276, No. 1, pp. 759-765.
Wolfe M. S. et al., "A substrate-based difluoro ketone selectively inhibits Alzheimer's Y-secretase activity," J.Med.Chem., 1998, vol. 41, pp. 6-9.
Taniguchi N. et al., "Implication of N-acetylglucosaminyltransferases III and V in cancer: gene regulation and signaling mechanism," Biochemica et Biophysica Acta 1999, vol. 1455, pp. 287-300.
Saito T. et al., "A secreted type of β1,6-N-acetylglucosaminyltransferase V (GnT-V) induces tumor angiogenesis without mediation og glycosylation," J.Biol.Chem., 2002, vol. 277, No. 19, pp. 17002-17008.
Taniguchi, Naoyuki et al., "Implication of GnT-V in Cancer Metastasis: A Glycomic Approach for Identification of a Target Protein and Its Unique Function as an Angiogenic Cofactor," *Glycoconjugate Journal* Nov.-Dec., vol. 18, Nos. 11-12, Nov. 2001, pp. 859-865.
Daniel, Paris et al., "Inhibition of Angiogenesis and Tumor Growth by Beta and Gamma-Secretase Inhibitors," *European Journal of Pharmacology* 514(1): 1-15, May 2005.
Barillari et al., "The Basic Residues of Placenta Growth Factor Type 2 Retrieve Sequestered Angiogenic Factors into a Soluble Form," American Journal of Pathology, vol. 152, No. 5, May 1998, pp. 1161-1166, American Society for Investigative Pathology, Bethesda, MD.

* cited by examiner

*Primary Examiner*—Ganapathirama Raghu
(74) *Attorney, Agent, or Firm*—Drinker Biddle & Reath LLP

(57) ABSTRACT

The present invention provides a peptide or protein having a neovascularization action and containing a basic amino acid cluster region of β1,6-N-acetylglucosaminyltransferase, a neovascularization accelerator containing the above-mentioned peptide or protein, a method of screening an inhibition substance for the above-mentioned peptide or protein, and a neovascularization inhibitor containing this inhibition substance.

9 Claims, 7 Drawing Sheets

(A)

(B)

SEQUENCE LISTING

```
<160> NUMBER OF SEQ ID NOS: 13

<210> SEQ ID NO 1
<211> LENGTH: 5
<212> TYPE: PRT
<213> ORGANISM: Homo sapiens

<400> SEQUENCE: 1

Thr Pro Trp Gly Lys
1               5

<210> SEQ ID NO 2
<211> LENGTH: 6
<212> TYPE: PRT
<213> ORGANISM: Homo sapiens

<400> SEQUENCE: 2

Asn Ile Pro Ser Tyr Val
1               5

<210> SEQ ID NO 3
<211> LENGTH: 17
<212> TYPE: PRT
<213> ORGANISM: Homo sapiens

<400> SEQUENCE: 3

Val Leu Asp Ser Phe Gly Thr Glu Pro Glu Phe Asn His Ala Asn Tyr
1               5                   10                  15
```

Ala

<210> SEQ ID NO 4
<211> LENGTH: 6
<212> TYPE: PRT
<213> ORGANISM: Homo sapiens

<400> SEQUENCE: 4

Asp Leu Gln Phe Leu Leu
 1               5

<210> SEQ ID NO 5
<211> LENGTH: 7
<212> TYPE: PRT
<213> ORGANISM: Homo sapiens

<400> SEQUENCE: 5

Asn Thr Asp Phe Phe Ile Gly
 1               5

<210> SEQ ID NO 6
<211> LENGTH: 2095
<212> TYPE: DNA
<213> ORGANISM: Homo sapiens
<220> FEATURE:
<221> NAME/KEY: CDS
<222> LOCATION: (156)...(2095)

<400> SEQUENCE: 6

```
ccggctgaag catcagaatg gaagtgagga aaggcaacca gctgacacag gagccagagt      60
gagaccagca gactctcaca ctcaacctac accatgaatt tgtgtctatc ttctacgcgt     120
taagagccaa ggacaggtga agttgccaga gagca atg gct ctc ttc act ccg       173
                                        Met Ala Leu Phe Thr Pro
                                          1               5 tgg aag ttg tcc tct cag aag ctg ggc ttt ttc ctg gtg act ttt ggc      221
Trp Lys Leu Ser Ser Gln Lys Leu Gly Phe Phe Leu Val Thr Phe Gly
             10                  15                  20 ttc att tgg ggt atg atg ctt ctg cac ttt acc atc cag cag cga act      269
Phe Ile Trp Gly Met Met Leu Leu His Phe Thr Ile Gln Gln Arg Thr
         25                  30                  35 cag cct gaa agc agc tcc atg ctg cgc gag cag atc ctg gac ctc agc      317
Gln Pro Glu Ser Ser Ser Met Leu Arg Glu Gln Ile Leu Asp Leu Ser
     40                  45                  50 aaa agg tac atc aag gca ctg gca gaa gaa aac agg aat gtg gtg gat      365
Lys Arg Tyr Ile Lys Ala Leu Ala Glu Glu Asn Arg Asn Val Val Asp
 55                  60                  65                  70 ggg cca tac gct gga gtc atg aca gct tat gat ctg aag aaa acc ctt      413
Gly Pro Tyr Ala Gly Val Met Thr Ala Tyr Asp Leu Lys Lys Thr Leu
                 75                  80                  85 gct gtg tta tta gat aac att ttg cag cgc att ggc aag ttg gag tcg      461
Ala Val Leu Leu Asp Asn Ile Leu Gln Arg Ile Gly Lys Leu Glu Ser
             90                  95                 100 aag gtg gac aat ctt gtt gtc aat ggc acc gga aca aac tca acc aac      509
Lys Val Asp Asn Leu Val Val Asn Gly Thr Gly Thr Asn Ser Thr Asn
        105                 110                 115 tcc act aca gct gtt ccc agc ttg gtt gca ctt gag aaa att aat gtg      557
Ser Thr Thr Ala Val Pro Ser Leu Val Ala Leu Glu Lys Ile Asn Val
    120                 125                 130 gca gat atc att aac gga gct caa gaa aaa tgt gta ttg cct cct atg      605
Ala Asp Ile Ile Asn Gly Ala Gln Glu Lys Cys Val Leu Pro Pro Met
135                 140                 145                 150
```

```
gac ggc tac cct cac tgt gag gga aag atc aag tgg atg aaa gac atg        653
Asp Gly Tyr Pro His Cys Glu Gly Lys Ile Lys Trp Met Lys Asp Met
                155                 160                 165 tgg cgt tca gat ccc tgc tac gca gac tat gga gtg gat gga tcc acc        701
Trp Arg Ser Asp Pro Cys Tyr Ala Asp Tyr Gly Val Asp Gly Ser Thr
            170                 175                 180 tgc tct ttt ttt att tac ctc agt gag gtt gaa aat tgg tgt cct cat        749
Cys Ser Phe Phe Ile Tyr Leu Ser Glu Val Glu Asn Trp Cys Pro His
        185                 190                 195 tta cct tgg aga gca aaa aat ccc tac gaa gaa gct gat cat aat tca        797
Leu Pro Trp Arg Ala Lys Asn Pro Tyr Glu Glu Ala Asp His Asn Ser
    200                 205                 210 ttg gcg gaa att cgt aca gat ttt aat att ctc tac agt atg atg aaa        845
Leu Ala Glu Ile Arg Thr Asp Phe Asn Ile Leu Tyr Ser Met Met Lys
215                 220                 225                 230 aag cat gaa gaa ttc cgg tgg atg aga cta cgg atc cgg cga atg gct        893
Lys His Glu Glu Phe Arg Trp Met Arg Leu Arg Ile Arg Arg Met Ala
                235                 240                 245 gac gca tgg atc caa gca atc aag tcc ctg gca gaa aag cag aac ctt        941
Asp Ala Trp Ile Gln Ala Ile Lys Ser Leu Ala Glu Lys Gln Asn Leu
            250                 255                 260 gaa aag aga aag cgg aag aaa gtc ctc gtt cac ctg gga ctc ctg acc        989
Glu Lys Arg Lys Arg Lys Lys Val Leu Val His Leu Gly Leu Leu Thr
        265                 270                 275 aag gaa tct gga ttt aag att gca gag aca gct ttc agt ggt ggc cct       1037
Lys Glu Ser Gly Phe Lys Ile Ala Glu Thr Ala Phe Ser Gly Gly Pro
    280                 285                 290 ctt ggt gaa tta gtt caa tgg agt gat tta att aca tct ctg tac tta       1085
Leu Gly Glu Leu Val Gln Trp Ser Asp Leu Ile Thr Ser Leu Tyr Leu
295                 300                 305                 310 ctg ggc cat gac att agg att tca gct tca ctg gct gag ctc aag gaa       1133
Leu Gly His Asp Ile Arg Ile Ser Ala Ser Leu Ala Glu Leu Lys Glu
                315                 320                 325 atc atg aag aag gtt gta gga aac cga tct ggc tgc cca act gta gga       1181
Ile Met Lys Lys Val Val Gly Asn Arg Ser Gly Cys Pro Thr Val Gly
            330                 335                 340 gac aga att gtt gag ctc att tac att gat att gta gga ctt gct caa       1229
Asp Arg Ile Val Glu Leu Ile Tyr Ile Asp Ile Val Gly Leu Ala Gln
        345                 350                 355 ttc aag aaa act ctt gga cca tcc tgg gtt cat tac cag tgc atg ctc       1277
Phe Lys Lys Thr Leu Gly Pro Ser Trp Val His Tyr Gln Cys Met Leu
    360                 365                 370 cga gtc ctt gat tca ttt ggt act gaa ccc gaa ttt aat cat gca aat       1325
Arg Val Leu Asp Ser Phe Gly Thr Glu Pro Glu Phe Asn His Ala Asn
375                 380                 385                 390 tat gcc caa tcg aaa ggc cac aag acc cct tgg gga aaa tgg aat ctg       1373
Tyr Ala Gln Ser Lys Gly His Lys Thr Pro Trp Gly Lys Trp Asn Leu
                395                 400                 405 aac cct cag cag ttt tat acc atg ttc cct cat acc cca gac aac agc       1421
Asn Pro Gln Gln Phe Tyr Thr Met Phe Pro His Thr Pro Asp Asn Ser
            410                 415                 420 ttt ctg ggg ttt gtg gtt gag cag cac ctg aac tcc agt gat atc cac       1469
Phe Leu Gly Phe Val Val Glu Gln His Leu Asn Ser Ser Asp Ile His
        425                 430                 435 cac att aat gaa atc aaa agg cag aac cag tcc ctt gtg tat ggc aaa       1517
His Ile Asn Glu Ile Lys Arg Gln Asn Gln Ser Leu Val Tyr Gly Lys
    440                 445                 450 gtg gat agc ttc tgg aag aat aag aag atc tac ttg gac att att cac       1565
Val Asp Ser Phe Trp Lys Asn Lys Lys Ile Tyr Leu Asp Ile Ile His
```

```
                455             460             465             470
aca tac atg gaa gtg cat gca act gtt tat ggc tcc agc aca aag aat       1613
Thr Tyr Met Glu Val His Ala Thr Val Tyr Gly Ser Ser Thr Lys Asn
                    475             480             485 att ccc agt tac gtg aaa aac cat ggt atc ctc agt gga cgg gac ctg       1661
Ile Pro Ser Tyr Val Lys Asn His Gly Ile Leu Ser Gly Arg Asp Leu
            490             495             500 cag ttc ctt ctt cga gaa acc aag ttg ttt gtt gga ctt ggg ttc cct       1709
Gln Phe Leu Leu Arg Glu Thr Lys Leu Phe Val Gly Leu Gly Phe Pro
        505             510             515 tac gag ggc cca gct ccc ctg gaa gct atc gca aat gga tgt gct ttt       1757
Tyr Glu Gly Pro Ala Pro Leu Glu Ala Ile Ala Asn Gly Cys Ala Phe
    520             525             530 ctg aat ccc aag ttc aac cca ccc aaa agc agc aaa aac aca gac ttc       1805
Leu Asn Pro Lys Phe Asn Pro Pro Lys Ser Ser Lys Asn Thr Asp Phe
535             540             545             550 ttc att ggc aag cca act ctg aga gag ctg aca tcc cag cat cct tac       1853
Phe Ile Gly Lys Pro Thr Leu Arg Glu Leu Thr Ser Gln His Pro Tyr
                555             560             565 gct gaa gtt ttc atc ggg cgg cca cat gtg tgg act gtt gac ctc aac       1901
Ala Glu Val Phe Ile Gly Arg Pro His Val Trp Thr Val Asp Leu Asn
            570             575             580 aat cag gag gaa gta gag gat gca gtg aaa gca att tta aat cag aag       1949
Asn Gln Glu Glu Val Glu Asp Ala Val Lys Ala Ile Leu Asn Gln Lys
        585             590             595 att gag cca tac atg cca tat gaa ttt acg tgc gag ggg atg cta cag       1997
Ile Glu Pro Tyr Met Pro Tyr Glu Phe Thr Cys Glu Gly Met Leu Gln
    600             605             610 aga atc aat gct ttc att gaa aaa cag gac ttc tgc cat ggg caa gtg       2045
Arg Ile Asn Ala Phe Ile Glu Lys Gln Asp Phe Cys His Gly Gln Val
615             620             625             630 atg tgg cca ccc ctc agc gcc cta cag gtc aag ctt gct gag ccc ggg       2093
Met Trp Pro Pro Leu Ser Ala Leu Gln Val Lys Leu Ala Glu Pro Gly
                635             640             645 cc                                                                    2095

<210> SEQ ID NO 7
<211> LENGTH: 16
<212> TYPE: PRT
<213> ORGANISM: Homo sapiens

<400> SEQUENCE: 7

Lys Ser Leu Ala Glu Lys Gln Asn Leu Glu Lys Arg Lys Arg Lys Lys
 1               5                  10                  15

<210> SEQ ID NO 8
<211> LENGTH: 24
<212> TYPE: DNA
<213> ORGANISM: Artificial Sequence
<220> FEATURE:
<223> OTHER INFORMATION: compound suppressing expression

<400> SEQUENCE: 8
gggagtgagg atgatgtagg gaag                                             24

<210> SEQ ID NO 9
<211> LENGTH: 24
<212> TYPE: DNA
<213> ORGANISM: Artificial Sequence
<220> FEATURE:
<223> OTHER INFORMATION: compound suppressing expression
```

```
<400> SEQUENCE: 9
atggggcaga ggaacttacg ttat                                          24

<210> SEQ ID NO 10
<211> LENGTH: 6
<212> TYPE: PRT
<213> ORGANISM: Homo sapiens

<400> SEQUENCE: 10

Gly Arg Gly Lys Arg Arg
1               5

<210> SEQ ID NO 11
<211> LENGTH: 6
<212> TYPE: PRT
<213> ORGANISM: Homo sapiens

<400> SEQUENCE: 11

Lys Arg Lys Arg Lys Lys
1               5

<210> SEQ ID NO 12
<211> LENGTH: 6
<212> TYPE: PRT
<213> ORGANISM: Homo sapiens

<400> SEQUENCE: 12

Phe Ser Gly Gly Pro Leu
1               5

<210> SEQ ID NO 13
<211> LENGTH: 5
<212> TYPE: PRT
<213> ORGANISM: Homo sapiens

<400> SEQUENCE: 13

His Phe Thr Ile Gln
1               5
```

GLYCOSYLTRANSFERASE GNT-V HAVING NEOVASCULARIZATION ACTION

FIELD OF THE INVENTION

The present invention relates to a secretory type glycosyltransferase, neovascularization action of N-acetylglucosaminyltransferase V (hereinafter, abbreviated as GnT-V), a basic amino acid cluster of the GnT-V relating to the neovascularization action, a utilization of GnT-V as neovascularization accelerator, a method of screening inhibitor for GnT-V and the basic amino acid cluster of GnT-V, a substance obtained by this screening method, a method of screening a substance inhibiting production of secretory type GnT-V, a substance obtained by this screening method, and a utilization of this substance as a neovascularization inhibitor.

BACKGROUND ART

In growth of cancers, factors such as fibroblast growth factor-2 (FGF-2), vascularendothelial growth factor (VEGF) and interleukin-8 (IL-8) and the like are involved. Production of these factors and cytokines is controlled by complicated mechanisms such as increase in gene expression, modification after translation of gene products, mutual action with extracellular matrix, and so on.

Many growth factors and receptors thereof are glycoproteins, and some of them are involved in neovascularization in tumor tissue. Recent studies using glycosyltransferase genes have revealed that change in the structure of an oligosaccharide of a growth factor receptor causes variation of intracellular signal transmission, leading to cancerization of cells (Yamashita, K., et al., J. Biol. Chem. 260, 3963-3969 (1985). Pierce, M & Arango, J., J. Biol. Chem. 261, 10772-10777 (1986). Zhu, T. Y., et al., J. Cancer Res. Clin. Oncol. 123, 296-299 (1997). Petretti, T., et al., Gut 46, 359-366 (2000)). It is suggested that $\beta$1,6-N-acetylglucosaminyltransferase V (GnT-V) catalyzing formation of $\beta(1,6)$ branch of asparagine sugar chain is the most important glycosyltransferase involved in metastasis of cancers (Demetriou, M., et al., J. Cell Biol. 130, 383-392 (1995). Dennis, J. W., et al., Science 236, 582-585 (1987)).

Neovascularization is an essential stage in progress of cancers such as metastasis and growth of cancers (Folkman, J., N. Eng. J. Med. 285, 1182-1186 (1971). Folkman, J. Ann. Surg. 175, 409-416 (1972)). A recent study using transgenic mouse lacking in GnT-V directly showed that GnT-V is essential for the growth of cancers and metastasis of cancers (Granovsky, M., et al., Nature Med. 6, 306-312 (2000)). Clinical studies have indicated increase in GnT-V activity in malignant tumors in lung and liver. It is shown that, in human lung cancer cells, GnT-V activity and size of tumors have a positive correlation (Dennis, J. W. & Laferte, S., Cancer Res. 49, 945-950 (1989)), and it is clarified that expression of GnT-V in human colon cancer cells is related with poor prognosis and metastasis (Murata, K., et al., Clin. Cancer Res. 6, 1772-1777 (2000)). However, detailed mechanisms of growth and metastasis of cancers via GnT-V have not been clarified yet.

Asparagine type sugar chains (Asn type sugar chains) found in glycoproteins are classified into three types of high mannose type, composite type and mixed type depending on its constituent sugars and type of branching. Biosynthesis of these Asn type sugar chains initiates first by one time transfer of sugar chain portions from a lipid intermediate into asparagine of a polypeptide chain under translation, in the lumen side of rough endoplasmic reticula. Thereafter, glucose and some mannoses are removed in rough endoplasmic reticula, however, some glycoproteins having an Asn type sugar chain localizing in rough endoplasmic reticula remain as they are, to leave high mannose type sugar chains. Other organelle glycoproteins, cell surface glycoproteins or secretory glycoproteins move to a Golgi body by vesicle transportation, and mannose is removed. In this Golgi body, N-acetylglucosamine is introduced by the action of N-acetylglucosaminyltransferase groups which are Golgi body enzymes to give a branch structure. By formation of this branch structure, conversion from a high mannose type sugar chain into a mixed type sugar chain and a composite type sugar chain initiates, and through introduction of fucose and introduction of galactose in a trans-Golgi region, finally, sialic acid is introduced to complete biosynthesis of Asn type sugar chains.

It is known that various enzymes act as a catalyst in each step of the sequential Asn type sugar chain synthesis. Six N-acetylglucosaminyltransferases are known as enzymes catalyzing a reaction of introducing transfer of N-acetylglucosamine in the formation of various branch structures of Asn type sugar chains in these steps. Schachter et al. (Brockhausen, I., et al., Biochem. Cell Biol., 66, 1134 (1988)) referred these six enzymes transferring N-acetylglucosamine into a core structure of a trimannosyl structure of Man $\alpha$1-3 (Man $\alpha$1-6) Man $\beta$1-4 GlcNAc $\beta$1-4 GlcNAc as GnT-I to GnT-VI. Of them, GnT-V is an enzyme relating to formation of $\beta(1,6)$ branch structure (-[GlcNAc $\beta(1,6)$ Man $\alpha(1,6)$ Man]-). It is known that the $\beta(1,6)$ branch structure is present in remarkably increased amount in cell transformation strains and tumor-forming cells (Pierce, M., et al., Biochem. Biophys. Res. Commun., 146, 679-684 (1987) and Arango, J., & Pierce, M., J., Cell. Biochem., 257, 13421-13427 (1982)). Further, it is shown that there is a relation between cancer metastasis ability of tumor-forming cells and emergence of a $\beta(1,6)$ branch (Hiraizumi, et al., A., Arch. Biochem. Biophys. 280, 9-19 (1990)). It is reported that in human, emergence of a $\beta(1,6)$ branch is accentuated in 50% of cases who received biopsy of breast carcinoma (Dennis, J. W., & Laferte, S. Cancer Res. 49, 945-950 (1989)). It is known that in any cases, emergence of a $\beta(1,6)$ branch structure is followed by increase in GnT-V activity. Thus, GnT-V is an enzyme which is important not only in catalysis of formation of a $\beta(1,6)$ branch structure in sugar chain biosynthesis route but also in relation with a easy transfer ability and malignancy of cancer cells.

SUMMARY

The present invention has been made in view of the above-mentioned conditions and an object thereof is to provide a new therapeutic target relating to cancer metastasis and growth which are most important problems in cancer therapy, and a therapeutic agent, a screening method of finding therapeutic agents, an evaluation method and a diagnosis method by clarifying a role played by a glycosyltransferase GnT-V on cancer metastasis and growth. Also, the present invention provides a new therapeutic idea that inhibition of secretion or expression of GnT-V suppresses not only cancer metastasis but also neovascularization which is a factor relating to cancer enlargement at metastasis site by providing a new biochemical concept that GnT-V promotes cancer metastasis and neovascularization. Further, the present invention provides a new drug design target in various ischemic diseases due to blood circulation disorder caused by vascular damage and the like, if neovascularization is regarded as a positive factor.

The present inventors have found that GnT-V which is one of glycosyltransferases has an action of accelerating neovascularization which is an initial regulation stage in cancer metastasis and subsequent cancer growth, as a new function utterly different from the original function as a glycosyltransferase. Namely, secretory type GnT-V and recombinant GnT-V which is purified promote in vitro and in vivo neovascularization at physiological concentration. Further, the present inventors have confirmed that a basic amino acid cluster region containing a significant amount of basic amino acids showing an action of releasing a fibroblast growth factor (FGF-2) from heparan sulfate proteoglycan (HSPG) on the surface of cells and in extracellular matrix is present in amino acid sequences of GnT-V. One of the present invention is a peptide or protein having an amino acid sequence in a basic amino acid cluster region of GnT-V, and a neovascularization accelerator containing this peptide or protein.

The present inventors have found that a glycosyltransferase GnT-V and a peptide having an amino acid sequence in a basic amino acid cluster region of this glycosyltransferase (basic peptide) accelerate neovascularization by releasing FGF-2 from HSPG on cancer cell surface, thereby promoting cancer metastasis and growth. On the basis of these findings, the present invention provides a method of screening a compound inhibiting neovascularization by GnT-V and the above-mentioned basic peptide, a compound obtained by said screening method, and a neovascularization inhibitor containing said compound. More specifically, the present invention provides a method of screening the following substances, a compound obtained by said screening method, and a neovascularization inhibitor containing said compound.

(a) A substance inhibiting a neovascularization action by GnT-V and a basic peptide (b) A substance which inhibits a protease cutting mature GnT-V present in a Golgi body to convert this into a secretory type GnT-V (c) A substance inhibiting gene expression of GnT-V (d) A substance inhibiting release of FGF-2 from heparan sulfate proteoglycan by GnT-V and a basic peptide (e) A substance inhibiting secretion of secretory type GnT-V out of a cell Namely, the present invention relates to (1) A peptide or protein having a neovascularization action and containing a basic amino acid cluster region of β1,6-N-acetylglucosaminyltransferase, (2) The peptide or protein according to (1), wherein the β1,6-N-acetylglucosaminyltransferase has the following properties:

(i) Action: N-acetylglucosamine is converted into α-6-D-mannoside using UDP-N-acetylglucosamine as a doner substrate;

(ii) Substrate specificity: If the substrate specificity when GnGn-bi-PA is a receptor is 100%, the substrate specificity when GnGnF-bi-PA is a receptor is about 78%, the substrate specificity when GnGnGn-tri-PA is a receptor is about 125%, and the substrate specificity when GnM-PA is a receptor is about 66%;

(iii) Optimum pH: 6.2 to 6.3;

(iv) Activity: $Mn^{2+}$ is not necessary for exertion of activity, and activity is not inhibited even in the presence of 20 mM EDTA;

(v) Molecular weight: About 73,000 (by SDS-PAGE in the absence of a reducing agent) and about 73,000 and about 60,000 (by SDS-PAGE in the presence of a reducing agent);

(vi) Km value: Km values for a receptor GnGn-bi-PA and a donor UDP-GlcNAc are 133 μM and 3.5 mM, respectively;

(vii) having the following peptide fragments:

(a) Thr-Pro-Trp-Gly-Lys, (b) Asn-Ile-Pro-Ser-Tyr-Val, (c) Val-Leu-Asp-Ser-Phe-Gly-Thr-Glu-Pro-Glu-Phe-Asn-His-Ala-Asn-Tyr-Ala, (d) Asp-Leu-Gln-Phe-Leu-Leu, and (e) Asn-Thr-Asp-Phe-Phe-Ile-Gly, (3) The peptide or protein according to (1), wherein the β1,6-N-acetylglucosaminyltransferase has an amino acid sequence containing at least an amino acid sequence encoded by SEQ ID NO: 6, or an amino acid sequence obtained by modification of one or more amino acids in this amino acid sequence, (4) The peptide or protein according to (1), wherein, in the basic amino acid cluster region, the number of basic amino acids accounts for 30% or more of the total number of amino acids in said region, (5) The peptide or protein according to (1), wherein the basic amino acid cluster region contains at least an amino acid sequence as depicted in SEQ ID NO: 7, or an amino acid sequence obtained by modification of one or more amino acids in this amino acid sequence, (6) A neovascularization accelerator containing the peptide or protein according to any of (1) to (5), (7) The neovascularization accelerator according to (6), wherein it is a wound healing agent, or an arteriosclerosis preventing and/or therapeutic agent, (8) A neovascularization inhibitor screening method, which comprises using the peptide or protein according to any of (1) to (5), (9) A neovascularization inhibitor screening method, which comprises using a cell capable of secreting the peptide or protein according to any of (1) to (5) expressed in the cell out of the cell,

(10) The screening method according to (9), wherein the cell is a cell in which the peptide or protein according to any of (1) to (5) can be highly expressed,

(11) A neovascularization inhibitor screening method, which comprises using a protease cutting a mature type β1,6-N-acetylglucosaminyltransferase anchored on a Golgi body membrane to convert this into a secretory type β1,6-N-acetylglucosaminyltransferase,

(12) The screening method according to (11), wherein the protease is β-secretase,

(13) The screening method according to (11), wherein the protease is γ-secretase,

(14) A compound showing a neovascularization inhibiting action in the screening method according to any of (8) to (13),

(15) A compound showing a neovascularization inhibiting action, wherein the compound suppresses expression of the peptide or protein according to any of (1) to (5),

(16) A compound showing a neovascularization inhibiting action, wherein the compound suppresses binding of the peptide or protein according to any of (1) to (5) to heparan sulfate proteoglycan,

(17) A neovascularization inhibitor comprising the compound according to any of (14) to (16),

(18) A neovascularization inhibitor comprising a compound having a γ-secretase inhibiting action,

(19) The neovascularization inhibitor according to (18), wherein the compound having a γ-secretase inhibiting action is a compound represented by the following formula (1):

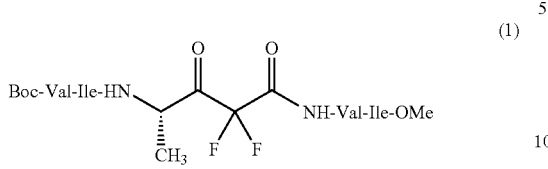

(1)

(wherein, Boc represents a butoxycarbonyl group, OMe represents a methoxy group, Val represents a valine, and Ile represents isoleucine),

(20) An antibody to the peptide or protein according to any of (1) to (5).

(21) An assay method for the peptide or protein according to any of (1) to (5), which comprises using the antibody according to (20),

(22) A detection kit for the peptide or protein according to any of (1) to (5), which comprises the antibody according to (20).

DETAILED DESCRIPTION

Figure 1:
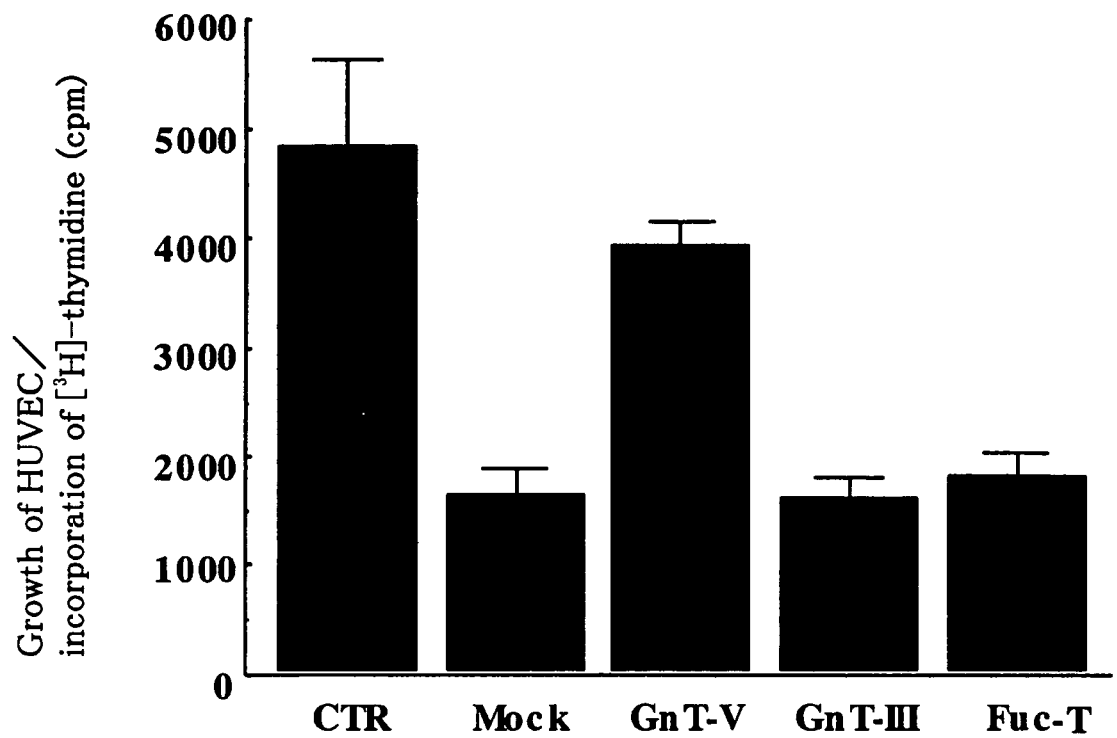
FIG. 1 is a view showing the differentiation and growth of HUVEC treated with culture solution of each cell, in terms of the amount of incorporation of [$^3$H]-thymidine as an index. CRT is a normal fresh medium used for culture of HUVEC.

The present invention provides a neovascularization accelerator containing a peptide or protein containing a basic amino acid cluster region of β1,6-N-acetylglucosaminyltransferase.

The above-mentioned β1,6-N-acetylglucosaminyltransferase may be a known substance, and it is, however, preferable that said enzyme has the following enzymological properties.

(a) Action: N-acetylglucosamine is converted into α-6-D-mannoside from UDP-N-acetylglucosamine;

(b) Substrate specificity: If the substrate specificity when GnGn-bi-PA is a receptor is 100%, the substrate specificity when GnGnF-bi-PA is a receptor is about 78%, the substrate specificity when GnGnGn-tri-PA is a receptor is about 125%, and the substrate specificity when GnM-PA is a receptor is about 66%;

(c) Optimum pH: 6.2 to 6.3;

(d) Activity: $Mn^{2+}$ is not necessary for exertion of activity, and activity is not inhibited even in the presence of 20 mM EDTA;

(e) Molecular weight: About 73,000 (by SDS-PAGE in the absence of a reducing agent) and about 73,000 and about 60,000 (by SDS-PAGE in the presence of a reducing agent);

(f) Km value: Km values for a receptor GnGn-bi-PA and a donor UDP-GlcNAc are 133 μM and 3.5 mM, respectively;

(g) having the following peptide fragments:
(i) Thr-Pro-Trp-Gly-Lys (SEQ ID NO: 1),
(ii) Asn-Ile-Pro-Ser-Tyr-Val (SEQ ID NO: 2),
(iii) Val-Leu-Asp-Ser-Phe-Gly-Thr-Glu-Pro-Glu-Phe-Asn-His-Ala-Asn-Tyr-Ala (SEQ ID NO: 3),
(iv) Asp-Leu-Gln-Phe-Leu-Leu (SEQ ID NO: 4), and
(v) Asn-Thr-Asp-Phe-Phe-Ile-Gly (SEQ ID NO: 5).

In the present invention, it is preferable to use GnT-V as the above-mentioned β1,6-N-acetylglucosaminyltransferase. GnT-V is an enzyme involved in the formation of β(1,6) branch structure (-[GlcNAc-β(1,6) Man-α (1,6) Man]-). Particularly, it is preferable that the above-mentioned β1,6-N-acetylglucosaminyltransferase has an amino acid sequence containing at least an amino acid sequence encoded by SEQ ID NO: 6, or an amino acid sequence obtained by modification of one or more amino acids in this amino acid sequence. It is more preferable that the above-mentioned enzyme has an amino acid sequence described in Nishikawa, et al., Biochem. Biophys. Res. Commun. 198, 318-327 (1994).

The above-mentioned enzyme can be easily obtained by known methods. For example, human origin GnT-V can be obtained by isolating GnT-V from a rat kidney and purifying this by the method described in Shoreibah, M., et al., J. Biol. Chem. 267, 2920-2927 (1992). It can be isolated and purified from concentrated liquid of a protein-free culture supernatant of human lung cancer (small cell carcinoma) origin QG cells by the method described in Japanese Patent Application Laid-Open (JP-A) No. 6-197756. The human lung cancer (small cell carcinoma) origin QG cell is named Human lung carcinoma SBM331, and internationally deposited with National Institute of Advanced Industrial Science and Technology (AIST), International Patent Organism Depositary (IPOD) under an acceptance number FERM BP-3967 on Aug. 18, 1992 based on Budapest Treaty.

The peptide or protein contained in the neovascularization accelerator of the present invention contains a basic amino acid cluster region of the above-mentioned β1,6-N-acetylglucosaminyltransferase, preferably GnT-V. The above-mentioned basic amino acid cluster region indicates a portion containing significant amount of basic amino acids in which the total number of amino acids is from about 5 to 50, preferably from about 8 to 40, more preferably from about 10 to 30. In the above-mentioned basic amino acid cluster region, it is preferable that the number of basic amino acids accounts for about 30% or more, preferably from about 35 to 95%, more preferably from about 40 to 90% of the total number of amino acids in the above-mentioned region.

More preferably, the above-mentioned basic amino acid cluster region contains at least an amino acid sequence as depicted in SEQ ID NO: 7. The above-mentioned basic amino acid cluster region may also contain at least an amino acid sequence obtained by modification of one or more amino acids in the amino acid sequence as depicted in SEQ ID NO: 7. Specifically, various modification type basic amino acid cluster regions are listed such as (a) a peptide obtained by adding one or more amino acids to the amino acid sequence as depicted in SEQ ID NO: 7, and maintaining a neovascularization action; (b) a peptide obtained by removing one or more amino acids from the above-mentioned amino acid sequence, and maintaining a neovascularization action; (c) a peptide obtained by substitution of one or more amino acids in the above-mentioned amino acid sequence by other amino acids, and maintaining a neovascularization action; further (d) a peptide having a combination of the above-mentioned amino acid addition modification, amino acid removal modification and amino acid substitution modification, and maintaining a neovascularization action; and the like. The number of amino acids subjected to the above-mentioned modification such as amino acid addition, removal and substitution is not particularly restricted, and determined depending on the object of the modification, and specifically, it is about 30% or less, preferably about 20% or less, more preferably about 10% or less of the number of amino acids in the basic amino acid cluster region. It is preferable that the above-mentioned amino acid modifications such as addition, removal and substitution are conducted on moieties other than basic amino acids.

The neovascularization accelerator according to the present invention may be the above-mentioned peptide or protein itself which is an active ingredient, however, usually, it is produced by mixing this active ingredient with a pharmaceutically acceptable carrier by a method known per se. [methods commonly used in the field of formulation technologies, for example, methods described in the Japanese Pharmacopoeia (for example, 13th edition) and the like]. The dosage form of the neovascularization accelerator according to the present invention includes, for example, oral preparations such as tablets (including coated tablets such as sugar-coated tablet or enteric tablet and multi-layer tablet), capsules (including soft capsules, microcapsules), powders, granules, syrups and the like, and parenteral preparations such as injections (for example, subcutaneous injection, intravenous injection, intramuscular injection, intraperitoneal injection and the like), external preparations (for example, intranasal preparation, percutaneous preparations such as ointment), suppositories (for example, rectal suppository, vaginal suppository and the like), pellets, drops, sustained-release preparations (for example, sustained-release microcapsule and the like) and the like. The neovascularization accelerator according to the present invention is preferably a parenteral preparation.

As the pharmaceutically acceptable carrier, various organic or inorganic carrier substances commonly used as raw materials in the formulation are used, and listed are excipients, lubricants, binders and disintegrating agents in solid preparations; and solvents, solubilizing agents, suspending agents, isotonizing agents, buffers, soothing agents and the like in liquid preparations. If necessary, additives in the formulation such as preservatives, antioxidants, coloring agents, sweetening agents and the like can also be used.

Preferable examples of the excipient include lactose, sucrose, D-mannitol, starch, crystalline cellulose, light silicic acid anhydride and the like. Preferable examples of the lubricant include magnesium stearate, calcium stearate, talc, colloidal silica and the like. Preferable examples of the binder include crystalline cellulose, sucrose, D-mannitol, dextrin, hydroxypropylcellulose, hydroxypropylmethylcellulose, polyvinylpyrrolidone and the like. Preferable examples of the disintegrating agent include starch, carboxymethylcellulose, carboxymethylcellulose calcium, crosscarmellose sodium, carboxymethyl starch sodium and the like.

Preferable examples of the solvent include water for injection, alcohol, propylene glycol, macrogol, sesame oil, corn oil and the like. Preferable examples of the solubilizing agents include polyethylene glycol, propylene glycol, D-mannitol, benzyl benzoate, ethanol, trisaminomethane, cholesterol, triethanolamine, sodium carbonate, sodium citrate and the like. Preferable examples of the suspending agent include surfactants such as stearyltriethanolamine, sodium lauryl sulfate, laurylaminopropionic acid, lecithin, benzalkonium chloride, benzethonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like. Preferable examples of the isotonizing agent include sodium chloride, glycerin, D-mannitol and the like. Preferable examples of the buffer include buffer solutions of phosphates, acetates, carbonates and citrates and the like. Preferable examples of the soothing agent include benzyl alcohol and the like. Preferable examples of the preservative include p-hydroxybenzoate ester, chlorobutanol, benzyl alcohol, phenethyl alcohol, dehydroacetic acid, sorbic acid and the like. Preferable examples of the antioxidant include sulfite, ascorbic acid and the like.

The neovascularization accelerator according to the present invention can be used for mammals (for example, human, mouse, rat, rabbit, dog, cat, bovine, horse, swine, monkey and the like).

The application of the neovascularization accelerator according to the present invention is not particularly restricted, and it is preferably used as a wound healing agent. The dose of the agent in this case is not determined indiscriminately since it varies depending on the type of disease conditions to be treated, the age and body weight of patient, symptoms, the seriousness of disease and the like, but it is about 0.01 to 100 mg/kg, preferably about 0.1 to 50 mg/kg. Particularly, it is preferable that the neovascularization accelerator according to the present invention is locally applied, in the form of liquid, ointment, cream, gel, cataplasm and the like, to a wound region and absorbed percutaneously to heal the wound. In the case of the external liquid preparation, the above-mentioned peptide or protein can be applied, for example, at a concentration of about 0.001 to 1000 mg/ml, further preferably of about 0.01 to 500 mg/ml. In the case of the external preparation other than liquid preparations, it is preferable that the above-mentioned peptide or protein is contained at a concentration of about 0.01 to 10 wt %.

The neovascularization accelerator according to the present invention can be used for treatment or prevention of aneurysm; arteriosclerosis such as coronary arteriosclerosis, cerebral arteriosclerosis or peripheral arteriosclerosis; peripheral artery obstruction, acute myocardial infarction (AMI), deep-vein thrombosis, pulmonary embolism, dissecting aneurysm, transient ischemic attack (TIA), apoplexy, and other obstruction-related disorders; unstable angina pectoris, disseminated intravascular coagulation (DIC), sepsis, surgical or infectious shock, postoperative and postpartum trauma, cardiopulmonary bypass surgical operation, incompatible blood transfusion, premature separation of the placenta, thrombotic thrombocytopenia purpura (TTP), acute or chronic renal diseases due to excess agglomeration such as snake venom and immune diseases, inflammation, hemolytic-uremic syndrome, symmetric peripheral necrosis, and bedsore. Further, the neovascularization accelerator according to the present invention can be used for enhancing the action of a thrombolytic agent and preventing re-obstruction, preventing re-obstruction after PTCA, preventing thrombocytopenia due to dialysis, preventing thrombosis caused by artificial blood vessels and organs.

When the neovascularization accelerator according to the present invention is used in the above-mentioned applications, the dose thereof is not determined indiscriminately since it varies depending on the application of the neovascularization accelerator, the type of disease conditions to be treated, the age and body weight of patient, symptoms, the seriousness of disease and the like, but it is about 0.01 to 100 mg/kg, preferably about 0.1 to 50 mg/kg, per day. Particularly, when administered intravenously, the dose thereof is about 0.01 to 5 mg/kg, preferably about 0.04 to 1.5 mg/kg, per day. It is desirable that this dose is administered 1 to 3 times per day.

In the neovascularization accelerator of the present invention, there can be used a concomitant drug not giving an adverse effect on the neovascularization action of the peptide or protein according to the present invention. The concomitant drug is not particularly restricted and when the neovascularization accelerator of the present invention is used as a treating and/or preventing agent for arteriosclerosis and the like, examples thereof include hypotensive agents, hypolipidemic agents, diuretics, thrombolytics and the like.

The timing of administration of the neovascularization accelerator according to the present invention and concomitant drug is not particularly restricted and these may be administered simultaneously, or administered at a time interval, to the subject to be administered. The dose of the concomitant drug may be advantageously determined according to clinically used dose, and can be appropriately selected depending on the target subject, age and body weight of the target subject, symptoms, time of administration, dosage form, administration route, combination and the like. The administration form of the concomitant drug is not particularly restricted, and it may be advantageous that the neovascularization accelerator according to the present invention and concomitant drug are combined at the time of administration.

The present invention provides an antibody to a peptide or protein containing a basic amino acid cluster region of β1,6-N-acetylglucosaminyltransferase. The above-mentioned antibody to a peptide or protein as an antigen may be any of a monoclonal antibody and polyclonal antibody. These antibodies can be produced according to known methods described, for example, in "Basic Experiment Method of Protein and Enzyme, 2nd revision (T. Horio ed., published by NANKO DO, 1994)" or "Method in Enzymology vol. 182 published by ACADEMIC PRESS, INC. 1990" and the like.

The present invention provides an assay method for the above-mentioned peptide or protein having a neovascularization action using these antibodies, and a detection kit for the above-mentioned peptide or protein having a neovascularization action using this assay method. Such an assay method and detection kit can be utilized in various applications. For example, neovascularization is an essential process in cancer metastasis, and therefore, a possibility of cancer metastasis can be found by measuring the presence or absence or the amount of the above-mentioned peptide or protein having a neovascularization action in the blood or cancer tissue of a patient with cancer using the assay method and detection kit according to the present invention.

In the assay method and detection kit according to the present invention, an antibody molecule itself may be used, and alternatively, $F(ab')_2$, Fab' or Fab fractions of the antibody molecule may be used. In the assay method and detection kit according to the present invention, an antibody of GnT-V or a fraction thereof is preferably used.

For the above-mentioned assay method and production of detection kit, known methods can be used. For example, as the method for quantifying the above-mentioned peptide or protein having a neovascularization action using the above-mentioned antibody, there are mentioned a measurement method in which the amount of an antibody corresponding to the antigen amount (for example, protein amount) in a test solution, the amount of an antigen or an antibody-antigen complex are detected by chemical or physical means, and this is calculated from the standard curve produced by using a standard solution containing an antigen in known amount, and other methods. More specifically, nephrometry, competition method, immunometric method or sandwich method, for example, are suitably used, and it is particularly preferable to use a sandwich method described later from the standpoint of sensitivity and specificity.

Specific embodiments of the assay method according to the present invention will be described below, however, the scope of the invention is not limited to these embodiments. Namely, there is exemplified, as the above-mentioned assay method, (i) a method of quantifying the above-mentioned peptide or protein having a neovascularization action in a test solution, wherein an antibody to the above-mentioned peptide or protein having a neovascularization action, a test solution, and the above-mentioned peptide or protein having a neovascularization action which has been labeled (hereinafter, referred to as simply "labeled peptide" in this column) are allowed to react competitively, and the proportion of the labeled peptide bound to the antibody is measured. Then, there is also mentioned (ii) a method of quantifying a peptide or protein having a neovascularization action in a test solution in which; the antibody to the above-mentioned peptide or protein having a neovascularization action is held on a carrier to provide insolubility; the antibody to the peptide or protein having a neovascularization action recognizing a region other than the above-mentioned insolubilized antibody is labeled; next, the test solution, the antibody insolubilized on the carrier, and the labeled antibody are reacted simultaneously or sequentially; then, the activity of the labeling agent arrested via the antigen (peptide or protein having a neovascularization action) on the carrier and/or the activity of the labeling agent not arrested on the carrier is measured. Further, as the method of assaying the peptide or protein having a neovascularization action of the present invention, detection by tissue stain and the like can also be conducted in addition to quantification of the peptide or protein having a neovascularization action using a monoclonal antibody to the peptide or protein.

As the labeling agent used in such an assay method according to the present invention, for example, radioactive isotopes, enzymes, fluorescent substances, light-emitting substances and the like are listed. As the above-mentioned radioactive isotope, for example, $^{125}$I, $^{131}$I, $^3$H or $^{14}$C and the like are used. As the above-mentioned enzyme, those which are stable and having large specific activity are preferable, and examples thereof include β-galactosidase, β-glucosidase, alkaline phosphatase, peroxidase, malic acid dehydrogenase and the like. As the above-mentioned fluorescent substance, for example, fluorescamine, fluorescein isothiocyanate and the like are used. As the above-mentioned light-emitting substance, for example, luminol, luminol derivatives, luciferin, lucigenin and the like are used. Furthermore, a biotin-avidin system can also be used for binding of an antibody or antigen with a labeling agent.

The present invention provides a neovascularization inhibitor. The neovascularization inhibitor according to the present invention is characterized in that it comprises one or more compounds selected from the group consisting of (a) a compound showing a neovascularization inhibiting action in the above-mentioned screening method using a peptide or protein having a neovascularization action, (b) a compound inhibiting the activity of a protease cutting a mature type β1,6-N-acetylglucosaminyltransferase anchored on a Golgi body membrane to convert this into a secretory type β1,6-N-acetylglucosaminyltransferase, (c) a compound suppressing expression of the above-mentioned peptide or protein having a neovascularization action, and (d) a compound suppressing binding of the above-mentioned peptide or protein having a neovascularization action to heparan sulfate proteoglycan. The neovascularization inhibitor according to the present invention may also contain (e) a compound inhibiting secretion of the above-mentioned peptide or protein having a neovascularization action out of a cell. The above-mentioned compound (e) can also be used in combination with one or more of the above-mentioned compounds (a) to (d). The above-mentioned compounds (a) to (e) will be described in detail below.

The above-mentioned compound (a) showing a neovascularization inhibiting action in a screening method using a peptide or protein having a neovascularization action can be obtained by a screening method as described below. Namely, as this screening method, there is mentioned a method in which neovascularization is observed in the case of the presence of the above-mentioned peptide or protein having a neovascularization action and a test substance in a system of observing neovascularization described in detail in examples, and it is compared with neovascularization in the case of the absence of a test substance. When neovascularization in the case of the presence of a test substance is smaller as compared with neovascularization in the case of the absence of a test substance in such a screening method, such a test substance is recognized as a substance showing a neovascularization inhibiting action. In this screening method, it is preferable to use GnT-V as the peptide or protein having a neovascularization action. More specifically, it may be advantageous that the total length of newly-produced blood vessels measurable from a micrograph in the case of the presence of a test substance is about 90% or less, preferably about 80% or less, more preferably about 70% or less, based on that in the case of the absence of a test substance. In a method of evaluating neovascularization described in detail in examples, it may be advantageous that the value in the case of the presence of a test substance is about 90% or less, preferably about 80% or less, more preferably about 70% or less, based on the value in the case of the absence of a test substance.

Here, the test substance used in the above-mentioned screening method is not particularly restricted, and may be a protein, or a compound of low molecular weight, or a compound of high molecular weight. It may also be a purified substance, or a mixture containing several co-existent compounds. Further, it may also be that of natural origin such as culture solution of a microorganism or a chemically synthesized substance. Moreover, the test substance may be a novel compound or a known compound. These are applied also in the following screening method.

The compound (b) inhibiting the activity of a protease cutting a mature type GnT-V anchored on a Golgi body membrane to release this from a Golgi body membrane and to convert this into a secretory type GnT-V can be easily obtained by a screening method using the above-mentioned protease. The screening method using the above-mentioned protease is not particularly restricted, and when the secretory type GnT-V generated by allowing the above-mentioned protease to act on the mature type GnT-V anchored on a Golgi body membrane in the presence of a test substance is smaller as compared with that obtained in the absence of a test substance, such a test substance is recognized as a compound inhibiting the activity of a protease. The above-mentioned test substance inhibiting the activity of a protease may also be screened in a test tube.

As the above-mentioned protease, for example, β-secretase and the like are listed. The amino acid sequence of the β-secretase is described in Vassar, R., et al., Science 286, 735-741 (1999) and the like, and easily available from information of GenBank accession number AF190725 and the like. As the above-mentioned protease, γ-secretase is also mentioned. γ-secretase cuts, at a transmembrane site, a carboxyl terminal peptide fragment, bound to a Golgi body membrane, of a 12 KD amyloid protein produced by cutting of an amino terminal of an amyloid-β-precursor by β-secretase (Tsai, J. Y., et al., Curr. Med. Chem. 9, 1087-1106 (2002)). Though the entity of γ-secretase is not clarified yet, it is believed to form a composite with presenilin bound to a Golgi body membrane and to cut amyloid protein (Wolfe, M. S., Curr. Top. Med. Chem. 2, 371-383 (2002)). The cell expressing γ-secretase can be obtained by known methods described in the above-mentioned literatures. For example, there can be used cells (e.g., PS-1 ΔE9) having a γ-secretase activity enhanced by highly expression of presenilin, and the like.

As the compound (b), for example, compounds having a γ-secretase inhibiting action are listed, and such compounds may have any structure providing they have an action of suppressing or inhibiting a γ-secretase activity. As the compound having a γ-secretase inhibiting action, there are listed compounds represented by the following formula (1):

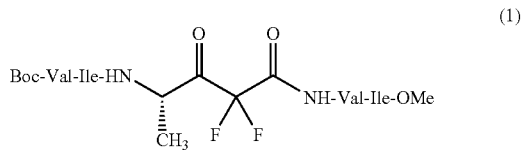

(1)

(wherein Boc represents a butoxycarbonyl group, OMe represents a methoxy group, Val represents valine, and Ile represents isoleucine).

Even derivatives of such compounds can be used as the neovascularization inhibitor in the present invention so long as they have a γ-secretase inhibiting action. As the derivative of the above-mentioned compound represented by the formula (1), there are listed, for example, (a) compounds in which a methyl group is substituted by a $C_2$-$C_6$ lower alkyl group, (b) compounds in which a butoxycarbonyl group which is a protective group at the amino terminal of valine is converted to a protective group of another amino group, (c) compounds in which a methoxy group which is a protective group at the carboxyl terminal of isoleucine is converted to a protective group of another carboxyl group, (d) compounds obtained by reducing the above-mentioned compound represented by the formula (1) to convert one or two carbonyl groups to a —CHOH— group, (e) compounds in which one or two valines are converted to another amino acid, preferably an aliphatic amino acid such as glycine, alanine, leucine or isoleucine and the like, (f) compounds in which one or two isoleucines are converted to another amino acid, preferably an aliphatic amino acid such as glycine, alanine, leucine or valine and the like, (g) compounds having a combination of two or more conversions in (a) to (f), and the like.

The compound (c) suppressing expression of the above-mentioned peptide or protein having a neovascularization action can be obtained by known methods. For example, a method using a promoter for expression of the above-mentioned peptide or protein having a neovascularization action and a reporter gene (T. Yokota, K. Arai, Biomanual series 4, YODO sha (1993)) is mentioned. Namely, the compound (c) can be obtained by a screening method using a transformant containing an introduced promoter for expression of the above-mentioned peptide or protein having a neovascularization action, preferably a promoter of a GnT-V gene, and an introduced reporter gene. More specifically, the above-mentioned promoter is connected to a translation region of the reporter gene to produce an expression vector, this expression vector is introduced into a host cell to produce a transformant, this transformant is cultured for a certain time, then, any amount of a test substance is added, and the amount of the reporter expressed by the cell after a certain time is measured as an enzyme activity, or as the amount of the expressed protein. More specifically, when the expression amount of the reporter gene in the presence of a test substance is smaller as compared with the expression amount of the reporter gene in the absence of a test substance, such a test substance can be recognized as a substance suppressing expression of the above-mentioned peptide or protein having a neovascularization action.

In the above-mentioned method, it is preferable to use a promoter region upstream of a GnT-V gene as the promoter for expression of the above-mentioned peptide or protein having a neovascularization action. Such a promoter can be obtained by cloning 5'-upstream region of a GnT-V gene from a genome of an HuCC-T1 cell (Saito, H., et al., Eur. J. Biochem. 233, 18-26 (1995)). The HuCC-T1 cell can be obtained from Japanese Cancer Resources Bank.

In the above-mentioned method, any genes encoding peptides or proteins may be used as the reporter gene so long as the activity or production amount of the expressed product (also including the production amount of mRNA) can be measured by persons skilled in the art. For example, chloramphenicol acetyltransferase (CAT), β-glactosidase (β-Gal), luciferase and the like can be utilized by measuring enzymatic activity. Secretory type growth hormone and the like can be utilized by measuring its production amount by an immune antibody reaction method and the like.

The above-mentioned expression vector can be obtained by inserting a translation region of the above-mentioned promoter and reporter genes into a replicable vector. The replicable vector is not particularly restricted, and pUC18 or pGEM-3Z and the like are listed as those replicable in *E. coli*. The above-mentioned expression vector is introduced into a host cell to produce a transformant. The host cell is not particularly restricted and can be selected appropriately depending on the type of the expression vector. Such transformation can be conducted by usual methods. As the transformant used in the present invention, those in which an expression vector is transiently introduced into a host are also used, in addition to those in which an expression vector is stably introduced into a host chromosome. Selection of the transformants in which an expression vector is stably introduced into a host chromosome can be conducted by transforming a host cell with a vector in which a selection marker gene is introduced into a vector to be introduced, or a vector containing a selection marker simultaneously with a vector to be introduced, and culturing the transformed cell in a medium in which only that having a selection marker can survive.

More preferably, a compound suppressing expression of the above-mentioned peptide or protein having a neovascularization action can be obtained by the following method. Namely, (a) DNA containing at least one of the following base sequence: 5'-GGGAGTGAGGATGATGTAGGGAAG-3' (SEQ ID NO: 8) and 5'-ATGGGGCAGAGGAACT-TACGTTAT-3' (SEQ ID NO: 9); (b) an Ets-1 protein or fragment thereof; and (c) a test substance are incubated together, and binding of the above-mentioned DNA (a) with an Ets-1 protein or fragment thereof is measured.

Transcription of a GnT-V gene is promoted by binding of an Ets-1 protein to a specific site shown in the above-mentioned sequence in a promoter region upstream of a GnT-V gene. The peptide or protein contains at least a basic amino acid cluster region of GnT-V. Therefore, a test substance inhibiting binding of DNA with an Ets-1 protein or fragment thereof in the above-mentioned sequence can suppress expression of the above-mentioned peptide or protein having a neovascularization action.

As the method of measuring binding of DNA with an Ets-1 protein or fragment thereof in the above-mentioned sequence, known methods may be used. As preferable embodiments of such a measuring method, a gel shift assay and supershift assay are listed and these methods will be illustrated in detail below.

The gel shift assay is conducted, for example, as described below. 5'-extended terminal of DNA in the above-mentioned sequence is labeled using [γ-$^{32}$P] DATP (available, for example, from Amersham). The resulted $^{32}$P labeled DNA (10,000 cpm) and a cut Ets-1 protein or nuclear extract which is in vitro transcribed/translated of MOLT4 cell are mixed together with a buffer containing 65 mM KCl, 25 mM Tris-HCl (pH 7.9), 6 mM $MgCl_2$, 0.25 mM EDTA and 10% glycerol so that the total volume is 20 ml. Subsequently, 2 µg of poly(dI-dC) (available, for example, from Sigma) is added to the reaction mixture. Then, the reaction mixture is cultured for 1 hour at room temperature. The resulted culture solution is added on 6% non-denaturing polyacrylamide gel (acrylamide:bisacrylamide=29:1), 0.5×TBE (1×TBE=89 mM Tris, 89 mM boric acid, 2 mM EDTA), then, electrophoresis is conducted at 40° C. and 150 V for 1 hour. After electrophoresis, the gel is dried by a gel drier, and then, exposed to an X-ray film (available, for example, from Kodak).

In the gel shift assay, the mobility manifested by the composite of DNA of the above-mentioned sequence with an Ets-1 protein or fragment thereof in electrophoresis using non-denaturing polyacrylamide gel decreases as compared with that manifested by DNA of the above-mentioned sequence not bound to an Ets-1 protein or fragment thereof. When a test substance is added in given amount to the above-mentioned reaction mixture, if a band of a composite of DNA of the above-mentioned sequence with an Ets-1 protein or fragment thereof is not observed or its band quantity decreases in the result of electrophoresis obtained by the above-mentioned procedure, the test substance can be judged to be a substance inhibiting binding of DNA of the above-mentioned sequence with an Ets-1 protein or fragment thereof.

The supershift assay is conducted in the same manner as for the gel shift assay, except that anti-Ets-1 IgG (available, for example, from Cambridge Research Biochemicals) not cross-reacting with a protein in other Ets family is added to the reaction mixture. In the supershift assay, the mobility manifested by the composite of DNA of the above-mentioned sequence with an Ets-1 protein or fragment thereof in electrophoresis using non-denaturing polyacrylamide gel decreases as compared with that manifested by DNA of the above-mentioned sequence not bound to an Ets-1 protein or fragment thereof, to a greater extent than in the gel shift assay. When a test substance is added in given amount to the above-mentioned reaction mixture, if a band of a composite of DNA of the above-mentioned sequence with an Ets-1 protein or fragment thereof is not observed or its band quantity decreases in the result of electrophoresis obtained by the above-mentioned procedure, the test substance can be judged to be a substance inhibiting binding of DNA of the above-mentioned sequence with an Ets-1 protein or fragment thereof.

The compound (d) suppressing binding of the above-mentioned peptide or protein having a neovascularization action to heparan sulfate proteoglycan may also be a compound which decreases affinity of the above-mentioned peptide or protein having a neovascularization action with heparan sulfate proteoglycan, as well as a compound preventing binding of the above-mentioned peptide or protein having a neovascularization action to heparan sulfate proteoglycan. The above-mentioned peptide or protein having a neovascularization action binds to heparan sulfate proteoglycan on the surface of a cell or on an extracellular matrix in competition with FGF-2 (fibroblast growth factor-2). Further, since the above-mentioned peptide or protein having a neovascularization action has higher affinity, than that of FGF-2, to heparan sulfate proteoglycan, FGF-2 bound to heparan sulfate proteoglycan is dissociated from heparan sulfate proteoglycan. Thus generated free FGF-2 stimulates an enthothelium to cause neovascularization. Therefore, if there is a compound which suppresses binding of the above-mentioned peptide or protein having a neovascularization action to heparan sulfate proteoglycan or which decreases affinity with heparan sulfate proteoglycan, FGF-2 can bind dominantly to heparan sulfate proteoglycan and the process of neovascularization as described above does not progress.

As the compound suppressing binding of the above-mentioned peptide or protein having a neovascularization action to heparan sulfate proteoglycan, for example, compounds blocking a basic amino acid cluster region of this peptide or protein, and the like are listed. Specific examples of such compounds include peptides and proteins containing an acidic amino acid cluster region containing a significant amount of acidic amino acids. Preferable as the above-mentioned acidic amino acid cluster region are portions containing significant amount of acidic amino acids having a total number of amino acids of about 5 to 50, preferably about 8 to 40, more preferably about 10 to 30. In the above-mentioned acidic cluster region, it is preferable that the number of acidic amino acids accounts for about 30% or more, preferably about 35 to 95%, more preferably about 40 to 90% of the total number of amino acids in the above-mentioned region. Preferable as the compound (d) are compounds suppressing binding of GnT-V to heparan sulfate proteoglycan.

The compound (e) inhibiting secretion of the above-mentioned peptide or protein having a neovascularization action out of a cell can be easily obtained by a screening method using a cell capable of secreting a peptide or protein having a neovascularization action expressed in a cell out of the cell. Specifically, there is mentioned a-screening method in which the above-mentioned cell is cultured in the presence of a test substance, and the amount of a peptide or protein having a neovascularization action secreted in the culture solution is measured. In such a screening method, if the amount of a peptide or protein having a neovascularization action decreases, the test substance can be a neovascularization inhibitor.

"Cell capable of secreting a peptide or protein having a neovascularization action expressed in a cell out of the cell" may be a cell which secretes a peptide or protein having a neovascularization action such as, for example, human colon cancer cell strain WiDr and the like, preferably a secretory type GnT-V. Particularly, preferable is a transformant containing an introduced gene encoding part or all of a peptide or protein having a neovascularization action, preferably GnT-V, the cell being capable of highly expressing a peptide or protein having a neovascularization action, preferably a secretory type GnT-V, as compared with a wild type cell. As this cell, there are listed a cell (PaCa-2/GnT-V cell) in which GnT-V is highly expressed by introduction of a GnT-V gene into a pancreas cancer cell MIA PaCa-2, a cell (KB/GnT-V cell) in which GnT-V is highly expressed by introduction of a GnT-V gene into an oral cavity cancer cell KB, and the like.

The amount of the peptide or protein having a neovascularization action secreted into culture solution can be measured directly using, for example, gel electrophoresis and the like. Further, the amount of the peptide or protein having a neovascularization action secreted into culture solution can also be measured indirectly by measuring the activity of the peptide or protein in culture solution, for example, $\beta$1,6-N-acetylglucosaminyltransferase activity.

The neovascularization inhibitor according to the present invention may be at least one compound itself among the above-mentioned compounds (a) to (e) which is an active ingredient, however, usually, it is produced by mixing the active ingredient with a pharmaceutically acceptable carrier by a method known per se. [methods commonly used in the field of formulation technologies, for example, methods described in the Japanese Pharmacopoeia (for example, 13$^{th}$ edition), and the like]. Here, as the pharmaceutically acceptable carrier, the same compounds as for the above-mentioned neovascularization accelerator are listed. As the dosage form of the neovascularization inhibitor according to the present invention, the same dosage forms as those of the above-mentioned neovascularization accelerator are exemplified, and particularly, the neovascularization inhibitor according to the present invention is preferably a parenteral preparation.

The neovascularization inhibitor according to the present invention can be used for mammals (for example, human, mouse, rat, rabbit, dog, cat, bovine, horse, swine, monkey and the like). The dose thereof is not determined indiscriminately since it varies depending on the type of active ingredients of neovascularization inhibitors, the type of disease conditions to be treated, the age and body weight of patients, symptoms, the seriousness of diseases, and the like.

The application of the neovascularization inhibitor according to the present invention is not particularly restricted and can be used as preventing and treating agents for various diseases including neovascularization, for example, tumors (for example, malignant melanoma, malignant lymphoma, digestive organ (e.g., stomach, intestine and the like) cancer, lung cancer, pancreas cancer, esophageal cancer, breast cancer, liver cancer, ovarian cancer, uterine cancer, prostate cancer, kidney cancer, bladder cancer, brain cancer, Kaposi's sarcoma, angioma, osteosarcoma, myosarcoma, angiofibroma and the like), inflammatory diseases (for example, rheumatic arthritis, psoriasis and the like), diabetic retinopathy, atherosclerosis (including abnormal angiopoiesis by formation of abnormal capillary network in atherosclerosis nest outer membrane) and the like. The neovascularization inhibitor of the present invention can be used also as an agent for treating eye hyperemia.

In the neovascularization inhibitor of the present invention, there can be used concomitant drugs not exerting an adverse effect on the neovascularization inhibition action of the above-mentioned compounds (a) to (e). As such concomitant drugs, there are listed, for example, antitumoragents, cachexy improving agents, antidiabetic agents other than insulin resistant improving agents, diabetic complication treating agents, antiobestic agents, hypotensive agents, hypolipidemic agents, diuretics and the like, and two or more of them may be combined. In use of the neovascularization inhibitor of the present invention, surgical therapy (operation) or radiation therapy may be conducted.

The timing of administration of the neovascularization inhibitor according to the present invention and concomitant drug, the dose of the concomitant drug, and the administration form of the concomitant drugs are the same as those in the case of the above-mentioned neovascularization accelerator.

EXAMPLES

The present invention will be illustrated in detail by the following examples, however, the scope of the invention is not limited to these examples.

Example 1

Acceleration of Neovascularization in a Nude Mouse by Metastasis of GnT-V Transformant Since expression of GnT-V shows a high correlation with metastasis and poor prognosis of colon cancer, transformants of β1,4-N-acetylglucosaminyltransferase III (GnT-III) and α1,6-fucosyltransferase (FucT) as a control were produced together with a stable transformant of GnT-V using a human colon cancer cell WiDr, and these were injected subcutaneously to a nude mouse to examine an influence exerted on cancer metastasis. The human colon cancer cell strain WiDr was cultured on an RPMI-1640 medium (manufactured by GIBCO BRL.) containing 10% fetal bovine serum (FBS) and antibiotics (penicillin and streptomycin). Transformation was conducted using a CELL FECTIN (registered trademark) reagent (manufactured by GIBCO BRL.), and transformation was conducted according to a method described in a manual of CELL FECTIN (registered trademark). Regarding transplantation of the above-mentioned transformed cancer cell to a nude mouse, $5 \times 10^5$ cells transformed with the above-mentioned glycosyltransferases were injected on the back of the nude mouse, and formation of cancer and neovascularization were visually observed one month after. Though the WiDr cell originally contains slight expression of the above-mentioned glycosyltransferase, acceleration of cancer metastasis was observed and remarkable neovascularization was observed in tumor tissue in the nude mouse transplanted with the GnT-V transformant as compared with the nude mouse transplanted with WiDr cells transformed with other glycosyltransferase genes. This result suggests that a cancer cell excessively expressing GnT-V secretes a certain factor accelerating neovascularization.

Example 2

Induction of Neovascularization by GnT-V Transformant

Acceleration of neovascularization by a GnT-V transformant was confirmed by a CAM (chorioallantoic membrane) assay using an embryo of a chicken fertilized egg. The CAM assay was conducted by a method of Yen et al. (Yen, L., et al., Oncogene 19, 3460-3469 (2000)) and a method of Bernardini (Bernardini, G., et al., Blood 96, 4039-4045 (2000)), both being slightly modified. CAM 8 days after fertilization of white Leghorn was used, and $1 \times 10^5$ cells thereof were inoculated on a collagen sponge and maintained for 4 hours. A 5 mm silicon ring was placed on CAM on the collagen sponge and maintained for 48 hours. It was found that invading of blood cells into the collagen sponge occurred only in the case of the GnT-V transformant among WiDr cells transformed with the glycosyltransferase gene described in Example 1. Also in cells obtained by transient transformation of a GnT-V gene into WiDr cells and noncancerous cells such as COS-1 cell and CHO cell, acceleration of neovascularization was observed in the CAM assay like with the above-mentioned GnT-V stable transformant. These results strongly suggest that a common mechanism exists for acceleration of neovascularization by expression of GnT-V.

Example 3

Induction of Neovascularization by Culture Solution of GnT-V Transformant

For in vitro evaluation of induction of neovascularization by a GnT-V transformant, the amount of synthesis of DNA of human umbilical vein epithelial cells (HUVEC) after stimulation with culture solution of a GnT-V transformant was measured by a method of Soker et al.(Soker, S., et al., J. Biol. Chem. 272, 31582-31588 (1997)). HUVEC was inoculated on a 96-well plate coated with type I collagen at a rate of $2 \times 10^3$ cells per well, and 24 hours later, the medium was substituted with an MCDB131 medium (not containing FBS and FGF-2) containing 0.1% fetal bovine serum albumin and a starved condition was maintained for 24 hours. The medium was substituted with culture solution of the WiDr cell transformed with the glycosyltransferase gene described in Example 1, and HUVEC was stimulated for 24 hours. HUVEC was maintained for 8 hours with [$^3$H]-thymidine (1 μCi/ml), and incorporation of [$^3$H]-thymidine into HUVEC was analyzed by MicroBeta-Counter (manufactured by Wallac) to measure the amount of synthesis of DNA. The result was shown as the mean value of assay results of 6 wells, and the standard deviation was measured. All experiments were repeated at least three times, and the same results were obtained. As apparent from FIG. 1, DNA synthesis of HUVEC stimulated with the culture solution of WiDr cells transformed with a GnT-V gene increased, however, the same effect was not observed in culture solution of WiDr cells transformed with other glycosyltransferase genes. These results indicate that the WiDr cell transformed with a GnT-V gene secretes a neovascularization factor derived from excess expression of GnT-V into culture solution.

Example 4

Influence of Recombinant GnT-V on Differentiation and Growth of HUVEC

Purification of a neovascularization factor present in culture solution of WiDr cells transformed with a GnT-V gene was conducted using various column chromatographies. The neovascularization activity of each fraction was evaluated by differentiation and growth of HUVEC described in Example 3. In heparin affinity chromatography, a fraction of high growth activity of HUVEC was eluted with 0.3 M NaCl. Since known growth factors such as FGF-1, FGF-2, VEGF, placenta-induced growth factor (PlGF) and hepatocyte growth factor (HGF) and the like are eluted with 0.8 to 1.5 M NaCl (Hauser, S. & Weich H. A., Growth Factor 9, 259-268 (1993). Gohda, E., et al., J. Clin. Invest. 81, 414-419 (1998). Marez, A., et al., Biochimie 69, 125-129 (1987). Risau, W., et al., The EMBO J. 7, 959-962 (1988). Rothenthal, R. A., et al., Growth Factor 4, 53-59 (1990)), the above-mentioned nature is utterly different from the natures of these known growth factors. The WiDr cell itself does not produce such a neovascularization factor. A fraction eluted with 0.3 M NaCl in heparin affinity chromatography was subjected to Western blot analysis using an anti-GnT-V antibody to find that the reaction of the anti-GnT-V antibody and the differentiation and growth activity of HUVEC are consistent each other, and the main protein having a differentiation and growth activity of HUVEC present in the fraction is GnT-V itself.

Figure 2:
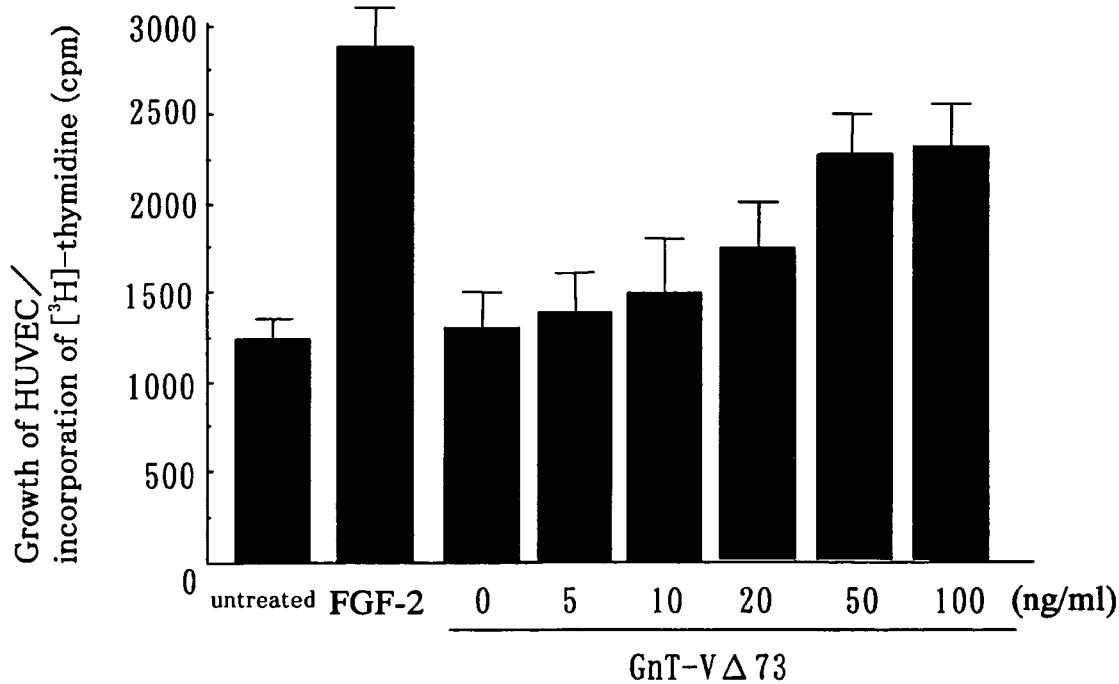
FIG. 2 is a view showing a relation between the addition amount of GnT-VΔ73 and the differentiation and growth of HUVEC.

Though it is known that GnT-V is secreted from cancer cells (Chen, L., et al., Glycoconjugate J. 12, 813-823 (1995)), like other glycosyltransferases (Gu, J., et al., J. Biochm. 113, 614-619 (1993). MaCaffery, G. & Jamison, J. C., Comp. Biochem. Physiol. B. 104, 91-94 (1993). Ugarte, M. A. & Rodriguez, P., J. Biochem. 23, 719-726 (1991)), the physiological significance of secretion of these glycosyltransferases is not known. For certifying a hypothesis that secretory type GnT-V itself induces differentiation and growth of HUVEC, a recombinant GnT-V, called GnT-VΔ73, maintaining a glycosyltransferase activity but lacking in transmembrane portion was produced. The GnT-VΔ73 which is a soluble recombinant GnT-V was prepared by a Baculovirus system according to a method disclosed in a literature of Sasai et al (Sasai, K., et al., Glycobiology (in press)). As shown in FIG. 2, by addition of GnT-VΔ73, recombinant GnT-V, differentiation and growth of HUVEC increased in addition amount-dependent manner. The concentration of the used GnT-VΔ73 was in the physiological range, and the concentration of GnT-V present in culture solution of GnT-V transformants was 140 ng/ml based on the specific activity of GnT-VΔ73. A mouse melanoma cell of B16-F10 had a high endogenous GnT-V activity, the culture solution of B16-F10 cells contained 70 ng/ml of GnT-V, and also the B16-F10 cell showed the same neovascularization activity in the CAM assay. Addition of recombinant Fuc-T did not show HUVEC growth accelerating activity at all. These results show that secretory type GnT-V in the physiological concentration range has an HUVEC growth accelerating activity.

Example 5

Analysis of Domain of GnT-V Involved in Differentiation

Figure 3:
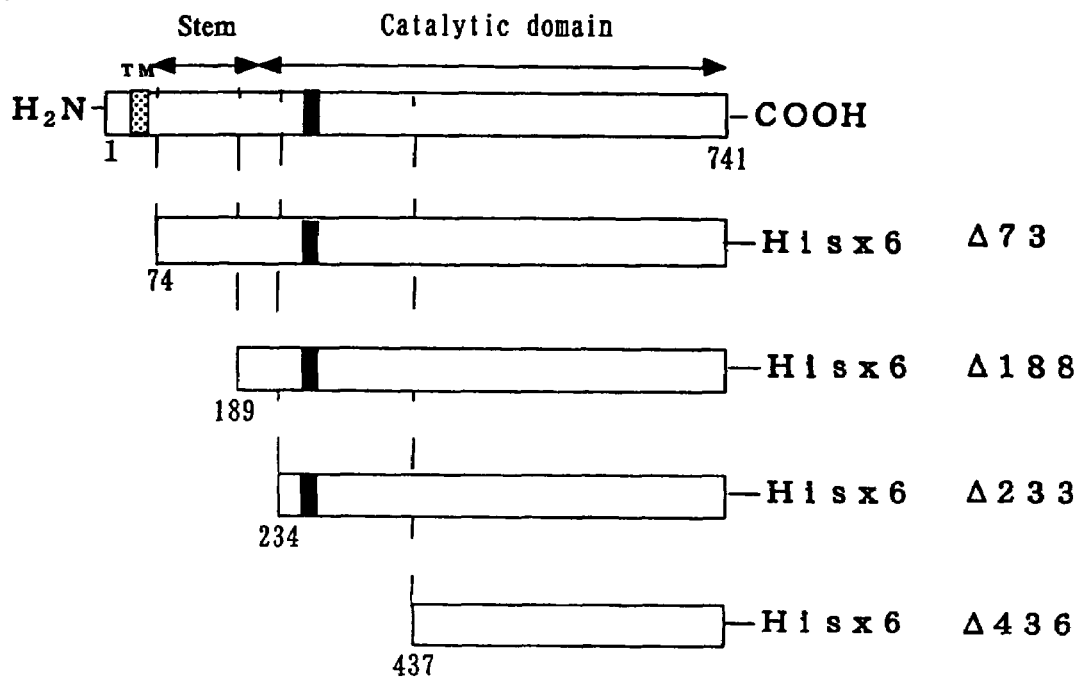
FIG. 3A is a schematic view of an amino acid sequence of each GnT-V-deficient variant.
FIG. 3B is a view showing an HUVEC differentiation and growth-accentuating action by each GnT-V-deficient variant.
Figure 3:
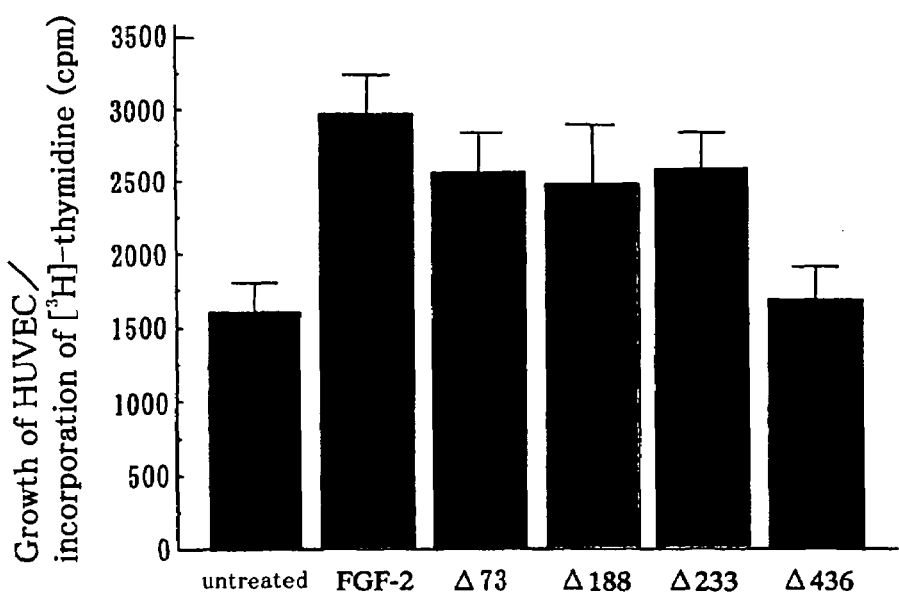

For clarifying which domain of GnT-V is involved in HUVEC growth accelerating activity, a GnT-V lacking variant shown in FIG. 3A was produced. The method of production of a GnT-VΔ188 plasmid is disclosed in a literature of Sasai et al (Sasai, K., et al., Glycobiology (in press)). A transfer plasmid having a GnT-VΔ233 gene was produced by binding a DNA fragment of 1521 base pairs encoding polyhistidine tag at the C-terminal and an amino acid sequence of from Glu234 to Leu741 of human GnT-V, obtained by cutting a GnT-VΔ188 plasmid with EcoRI and EagI, to an EcoRI-EagI site of a transfer vector pAcGP67-A (manufactured by PharMingen). A transfer plasmid having a GnT-VΔ436 gene was produced by binding a DNA fragment of 912 base pairs encoding polyhistidine tag at the C terminal and an amino acid sequence of from Ile437 to Leu741, of human GnT-V, obtained by cutting a GnT-VΔ188 plasmid with EcoRV and EagI, to an EcoRV-EagI site of a transfer vector pAcGP67-A. For production of a recombinant Baculovirus, an insect cell Sf21 was transformed with the transfer plasmid obtained above according to a method known in a literature (Ikeda, Y., et al., J. Biochem. 128, 609-619 (2000)). The recombinant glycosyltransferase derived from the transformed Sf21 cell was purified by $Ni^{2+}$-chelating affinity chromatography according to a method disclosed in a literature of Sasaki et al (Sasai, K., et al., Glycobiology (in press)).

As shown in FIG. 3B, GnT-VΔ73, GnT-VΔ188 and GnT-VΔ233 variants had an HUVEC growth and differentiation accentuation action, however, GnT-VΔ436 did not have an HUVEC growth and differentiation accentuation action. Though GnT-VΔ73 and GnT-VΔ188 had a glycosyltransferase activity, GnT-VΔ233 and GnT-VΔ436 had no glycosyltransferase activity. These results suggest that the HUVEC growth accelerating activity is present in a region corresponding to an amino acid sequence of from 234 to 436 of GnT-V and this region does not contain a region involved in a glycosyltransferase activity.

Example 6

Figure 4:
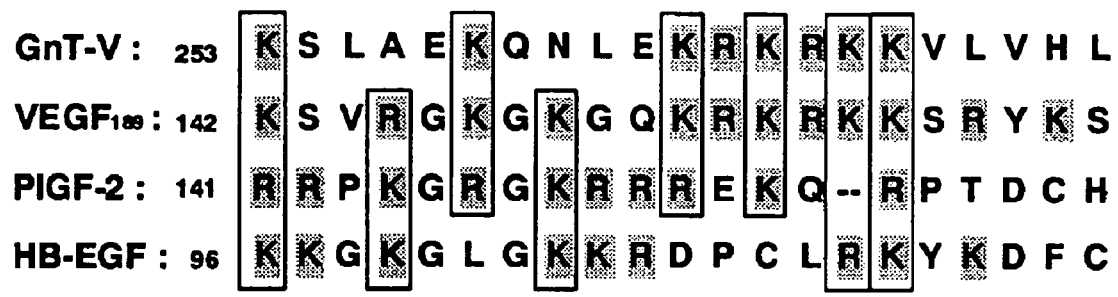
FIG. 4 is a view showing similarity between an amino acid sequence of a basic cluster region of GnT-V and amino acid sequences of VEGF$_{189}$, P1GF-2 and HB-EGF.

Identification of Basic Amino Acid Cluster Region of GnT-V Inducing Neovascularization An amino acid sequence of from 254 to 269 of human GnT-V is a sequence of Lys-Ser-Leu-Ala-Glu-Lys-Gln-Asn-Leu-Glu-Lys-Arg-Lys-Arg-Lys-Lys (SEQ ID NO: 7) in which basic amino acids form a cluster, and a sequence fairly resembling this sequence is observed in an amino acid sequence of from 142 to 157 of $VEGF_{189}$ (Hauser, S. & Weich H. A., Growth Factor 9, 259-268 (1993)) (see, FIG. 4). This amino acid cluster region is also kept in PlGF-2 and heparin binding type epidermis growth factor-like growth factor (HB-FGF) (see, FIG. 4), and acts as a heparin-binding motif (Hauser, S. & Weich, H. A., Growth Factor 9, 259-268 (1993)). Barillari et al. have reported that a basic peptide having a sequence of Gly-Arg-Gly-Lys-Arg-Arg (SEQ ID NO: 10) derived from PlGF-2 release FGF-2 from heparan sulfate proteoglycan (HSPG) on cell surface and/or extracellular matrix, to induce growth of epidermal cells (Barillari, G., et al., American J. Patho. 152, 1161-1166 (1998)).

A basic peptide (KRKRKK peptide) composed of Lys-Arg-Lys-Arg-Lys-Lys (SEQ ID NO: 11) which is an amino acid sequence of from 264 to 269 and a non-basic control peptide (FSGGPL peptide) composed of Phe-Ser-Gly-Gly-Pro-Leu (SEQ ID NO: 12) which is an amino acid sequence of from 291 to 296, of GnT-V, were synthesized, and an influence of these peptides on growth of HUVEC was examined. The peptide was synthesized by a peptide synthesizer A432 (manufactured by Applied Biosystems), and purified by reverse phase HPLC, then, its molecular weight and degree of purification were confirmed by MALDI TOF-MS (Voyager- DE (registered trademark) RP; manufactured by PerSeptive Biosystems). The concentration of FGF-2 was measured by a known method (Barillari, G., et al., American J. Patho. 152, 1161-1166 (1998)). That is, HUVEC was inoculated on a 12-well plate coated with collagen at a rate of $5 \times 10^4$ cells per well, and washed twice with PBS, then, the medium was substituted with MCDB 131/0.1% BSA (0.5 ml/well), and the plate was maintained at 4° C. for 2 hours on a plate rotation table in the presence or absence of GnT-VΔ73, GnT-VΔ436, KRKRKK peptide or FSGGPL peptide, together with heparin. After centrifugation at 4° C. and 3000 rpm for 5 minutes, the supernatant was collected, the concentration of FGF-2 in the supernatant was measured in an FGF-2 ELISA system (manufactured by R&D Systems) according to a manual of this system.

Figure 5:
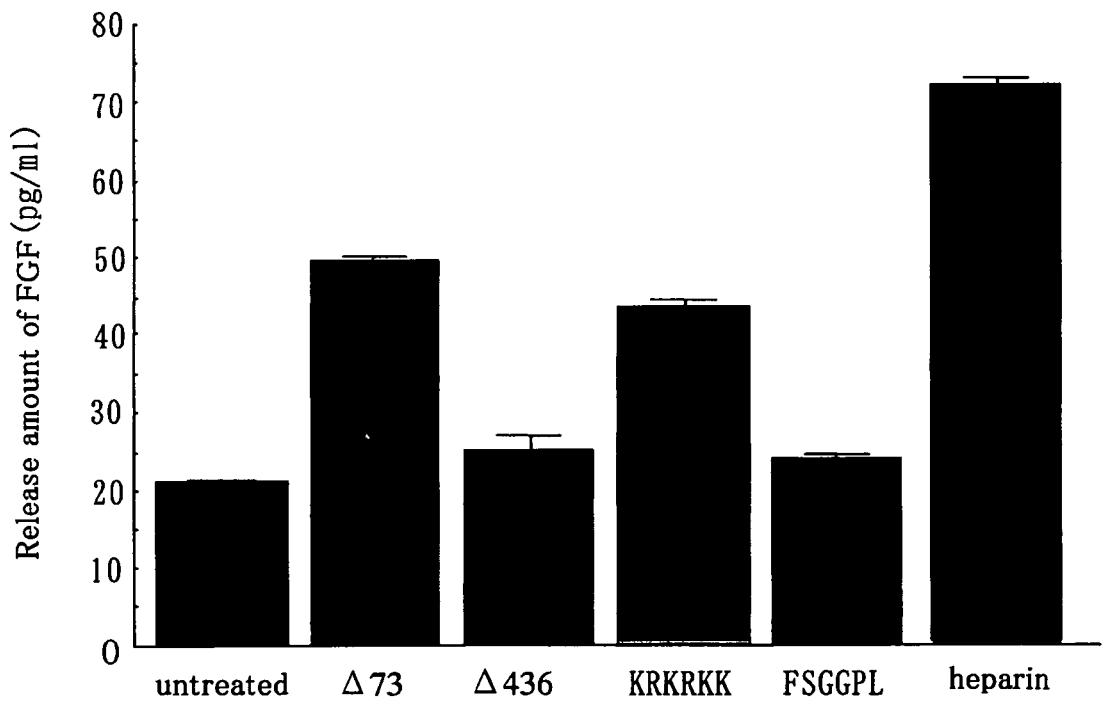
FIG. 5 is a view showing the amount of discharge of FGF-2 by various deficient variants of GnT-V and a synthetic peptide.
Figure 6:
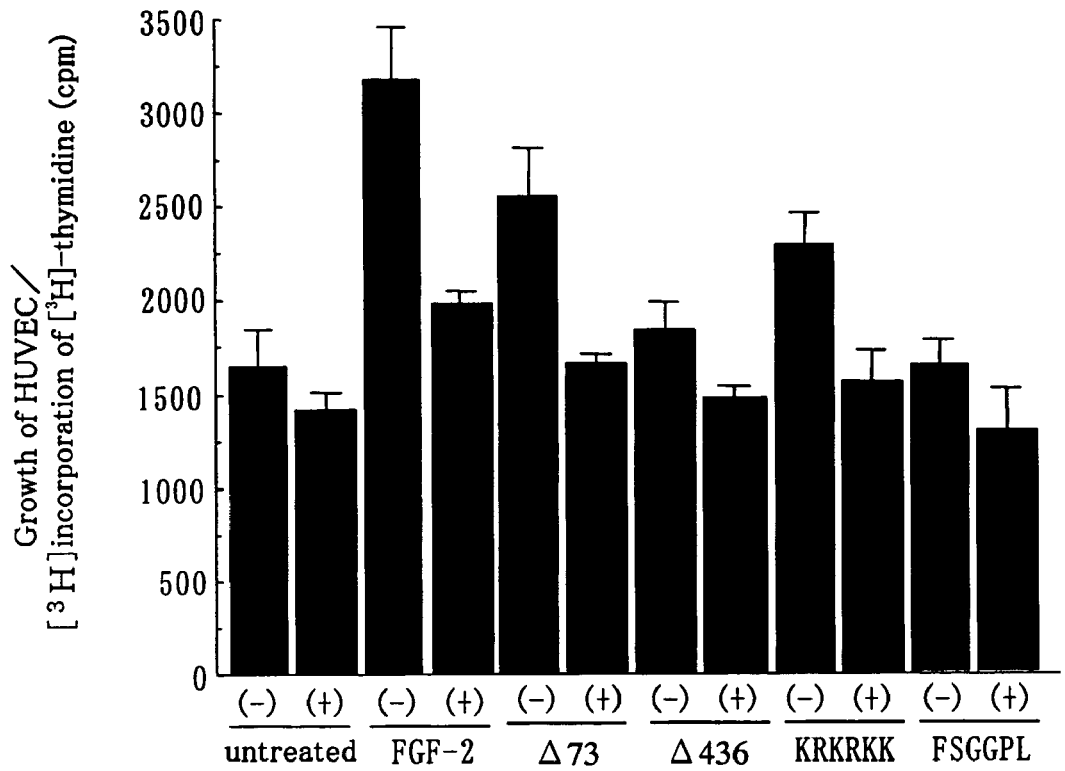
FIG. 6 is a view showing an HUVEC differentiation and growth-accentuating action by various deficient variants of GnT-V and a synthetic peptide.
Figure 7:
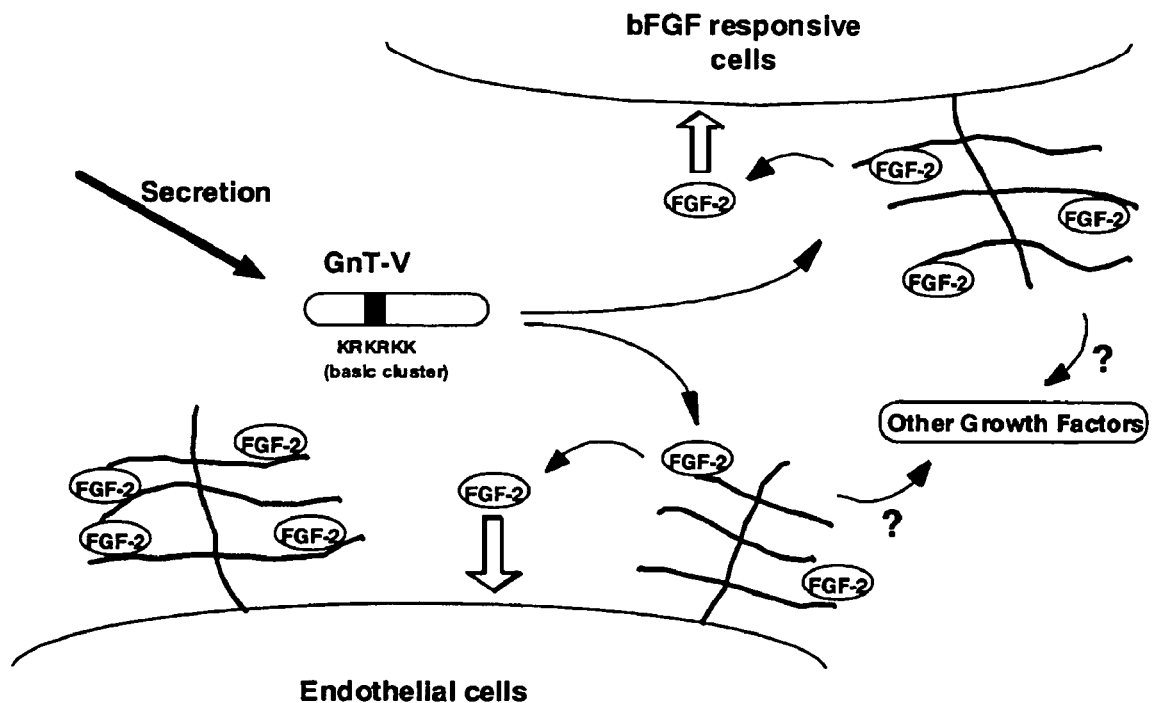
FIG. 7 is a schematic view showing induction of cancer neovascularization by GnT-V. Secretory type GnT-V containing a basic amino acid cluster region binds, in competition with FGF-2, to HSPG on the surface of a cell, and resultantly, release of FGF-2 occurs, to stimulate a FGF-2 receptor on the target cell.

As described above, various deficient variants of GnT-V and synthetic peptides were added at 4° C. to culture solution of HUVEC, and the amount of FGF-2 released from HSPG on HUVEC was measured. As a result, as shown in FIG. 5, GnT-VΔ73 and KRKRKK peptide released FGF-2, however, GnT-VΔ436 and FSGGPL peptide did not affect release of FGF-2. Like GnT-VΔ73, also GnT-VΔ188 and GnT-VΔ233 released FGF-2. Similarly, heparin (Biard, A., et al., Proc. Natl. Acad. Sci. USA 85, 2324-2328 (1988)) which is known to release the HSPG binding molecule by competition with a heparin binding site of the HSPG binding molecule induced release of FGF-2. Phosphorylation of an FGF receptor on HUVEC by stimulation of released FGF-2 was also confirmed. As shown in FIG. 6, the KRKRKK peptide accelerated growth of HUVEC at the same degree as GnT-VΔ73, however, this effect was completely suppressed by an anti-FGF-2 neutralization antibody added simultaneously. These results suggest that a basic amino acid cluster region of GnT-V is sufficient for an HUVEC growth accelerating activity, and a GnT-V protein releases FGF-2 from HSPG on an endothelium by the action of a basic portion of this protein, to accelerate neovascularization.

Example 7

In vivo Neovascularization by GnT-V Protein

Induction of neovascularization by GnT-V was confirmed also by other in vitro neovascularization assays such as a capillary-like tube formation assay (Ashoton, A. W., et al., J. Biol. Chem. 274, 35562-35570 (1999)) and a migration assay (Zeng, H., et al., J. Biol. Chem. 276, 3271-3279 (2001)) using HUVEC. For confirming ex-vivo neovascularization activity of GnT-V, a CAM assay using a GnT-VΔ73 protein was conducted. The GnT-VΔ73 induced neovascularization of chicken microvessels like FGF-2, and the KRKRKK peptide induced neovascularization likewise, however, induction of neovascularization by GnT-VΔ73 and KRKRKK peptide was inhibited by treatment with an anti-FGF-2 neutralization antibody. In contrast, GnT-VΔ436 and FSGGPL peptide did not have a neovascularization activity. These results indicate that secretory type GnT-V and the KRKRKK peptide derived from GnT-V induce neovascularization via the action of FGF-2, however, the basic region of GnT-V causes release of FGF-2 from HSPG on an endothelium, in view of the results of the HUVEC differentiation and growth assay.

Example 8

Analysis of Cut Site of Mature Type GnT-V Protein

Figure 8:
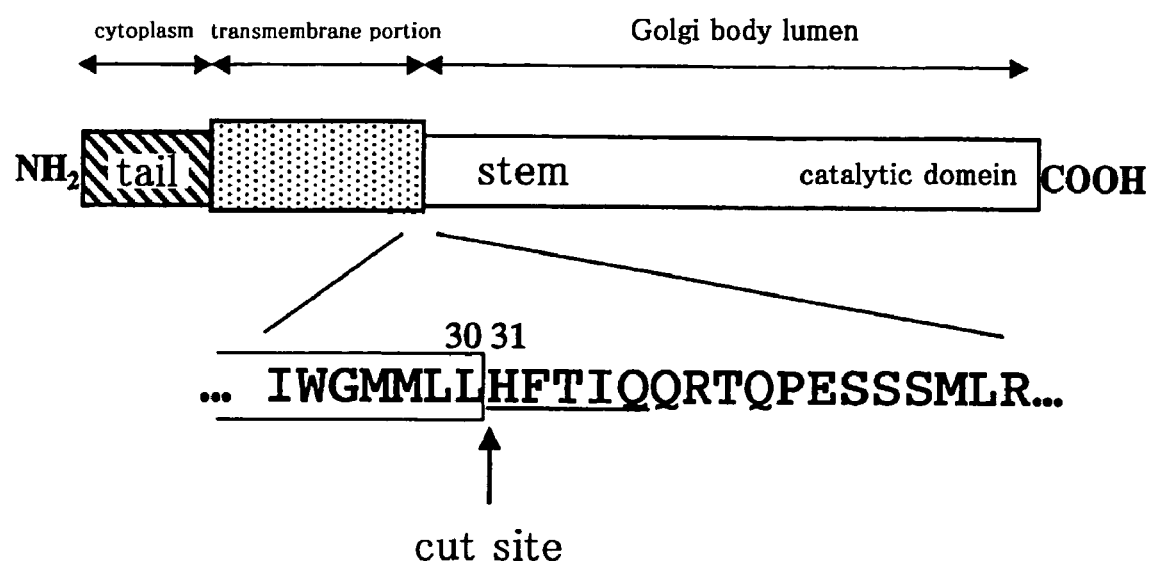
FIG. 8 is a view showing the outline of the structure of a mature type GnT-V. A cut part when the mature type GnT-V is cut in the lumen of a Golgi body to be converted into a secretory type GnT-V is enlarged, and its amino acid sequence is shown.

As shown in FIG. 8, a mature type GnT-V has at the amino terminal side a transmembrane portion composed of a hydrophobic amino acid, and therefore, it is believed that the amino terminal side is anchored on a membrane of a Golgi body which is an intracellular organelle, and a catalyst portion involved in a glycosyltransferase activity is present in the lumen of a Golgi body. Since it is guessed that a mature type GnT-V is cut in the lumen of a Golgi body to be converted into a secretory type GnT-V, and secreted out of the cell through a secretion route, an amino acid sequence at the amino terminal of the secretory type GnT-V secreted out of the cell was determined, and the cut part was analyzed.

A GnT-V gene was introduced into a pancreas cancer cell MIA PaCa-2 and GnT-V was highly expressed and this cell (PaCa-2/GnT-V) was cultured to obtain 1500 ml of serum-free culture solution. Cell transformation and culturing of transformants were conducted according to the methods described in Example 1. This culture solution was precipitated with saturated ammonium sulfate, and the recovered ammonium sulfate precipitate was dissolved in 10 ml of PBS (phosphate buffer saline), and desalted in a PD-10 column (Code Number: 17-0851-01, Amersham Pharmacia Biotech), and simultaneously, the buffer solution was substituted with 50 mM Tris-HCl (pH 7.5). Subsequently, purification thereof was conducted by affinity chromatography using, as a ligand, a mouse monoclonal antibody 24D11 of GnT-V produced according to the known methods described in "Basic Experiment Method of Protein and Enzyme, 2nd revision (T. Horio ed., published by NANKO DO, 1994)" and "Method in Enzymology vol. 182 published by ACADEMIC PRESS, INC. 1990".

A column containing Protein A Sepharose 4B as a carrier was equilibrated with 50 mM Tris-HCl (pH 7.5) to allow a secretory type GnT-V to be adsorbed on the column, then, the secretory type GnT-V was eluted with 50 mM Tris-HCl (pH 7.5) containing 0.05% of TFA (trifluoroacetic acid). The eluate was fractionated by SDS-polyacrylamide gel electrophoresis to find a main band at a portion corresponding to a molecular weight of secretory type GnT-V of about 100 kD.

The amino acid sequence at the amino terminal of secretory type GnT-V extracted from the gel was determined by a method known in the literature. As a result, as shown in FIG. 8, the sequence at the amino terminal of secretory type GnT-V was determined to be His-Phe-Thr-Ile-Gln- (SEQ ID NO: 13), however, this amino acid sequence was consistent with an amino acid sequence of from 31 to 35 in the amino acid sequence of GnT-V encoded by SEQ ID NO: 6, therefore, it was found that secretory type GnT-V is produced by cutting between a 30th amino acid leucine and a 31st amino acid histidine in mature type GnT-V.

Example 9

Identification of Protease Involved in Production of Secretory Type GnT-V and Screening of Substance Inhibiting Production of Secretory Type GnT-V Since the cut portion in the secretory type GnT-V analyzed in Example 8 is present at the boundary between a transmembrane site and a Golgi body lumen site of GnT-V shown in FIG. 8, a γ-secretase bound to a Golgi body membrane was hypothesized as a protease involved in cutting.

A nerve cell SK-N-SH having a high γ-secretase activity and manifesting strong expression of endogenous GnT-V, in which variant presenilin-1 was highly expressed, was used, and this cell was cultured in the method described in Example 1, and the influence of γ-secretase on production of secretory type GnT-V was examined. The amount of secretion of GnT-V in the culture solution was quantified by concentrating 10-fold the culture solution and measuring an enzymatic activity using HPLC according to the method described in JP-A No. 6-197756.

Figure 9:
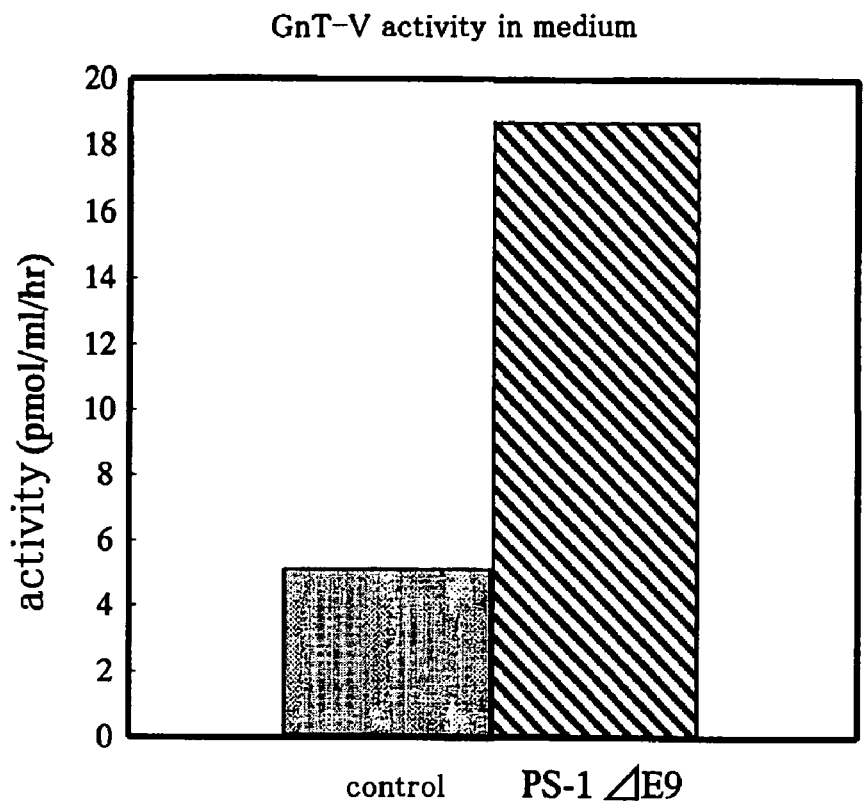
FIG. 9A shows a GnT-V activity of a cell (PS-1 ΔE9) in which variant presenilin-1 is highly expressing and a cell (control) in which variant presenilin-1 is not highly expressing, in culture solution.
FIG. 9B shows a ratio of a GnT-V activity in culture solution (extracellular) to a GnT-V activity in a cell, of the above-mentioned two kinds of cells.
Figure 9:
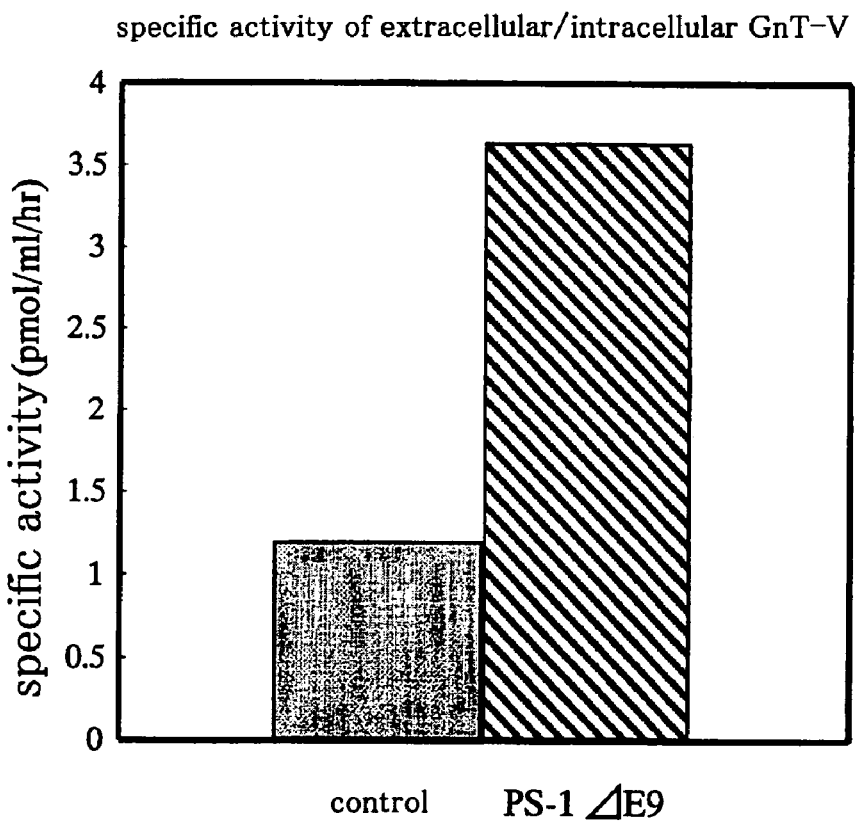

As shown in FIG. 9A, it was confirmed that the GnT-V activity in culture solution of cells (PS-1 ΔE9) in which variant presenilin-1 had been highly expressed was about 4-fold of that of cells (control) in which variant presenilin-1 had not been highly expressed, and γ-secretase cuts a mature type GnT-V to produce a secretory type GnT-V. Further, as shown in FIG. 9B, it was confirmed that, in the case of the cells (PS-1 ΔE9) in which variant presenilin-1 had been highly expressed, the ratio of the GnT-V activity in culture solution (extracellular) to that in cell was about 3.5, which was about 3-fold higher than a ratio in the case of the cells in which variant presenilin-1 had not been highly expressed of about 1.2, and production and secretion of secretory type-GnT-V were accelerated by high expression of a γ-secretase activity.

Figure 10:
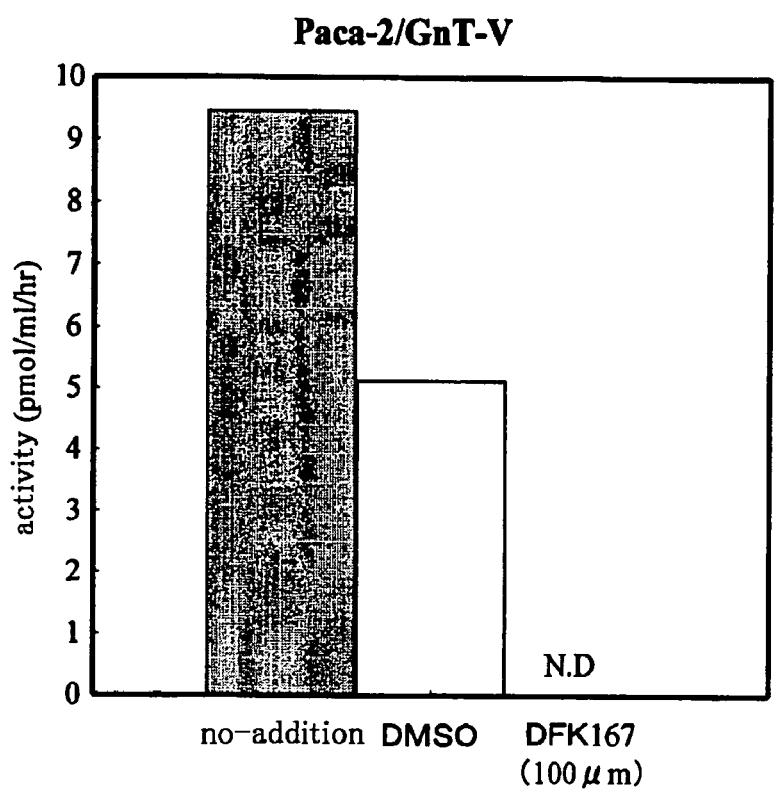
FIG. 10A shows a value of GnT-V activity in culture solution of a PaCa-2/GnT-V cell in the case of no addition, in the case of addition of DMSO, and in the case of addition of DFK167 dissolved in DMSO.
FIG. 10B shows a value of GnT-V activity in culture solution of a KB/GnT-V cell in the above-mentioned three cases.
Figure 10:
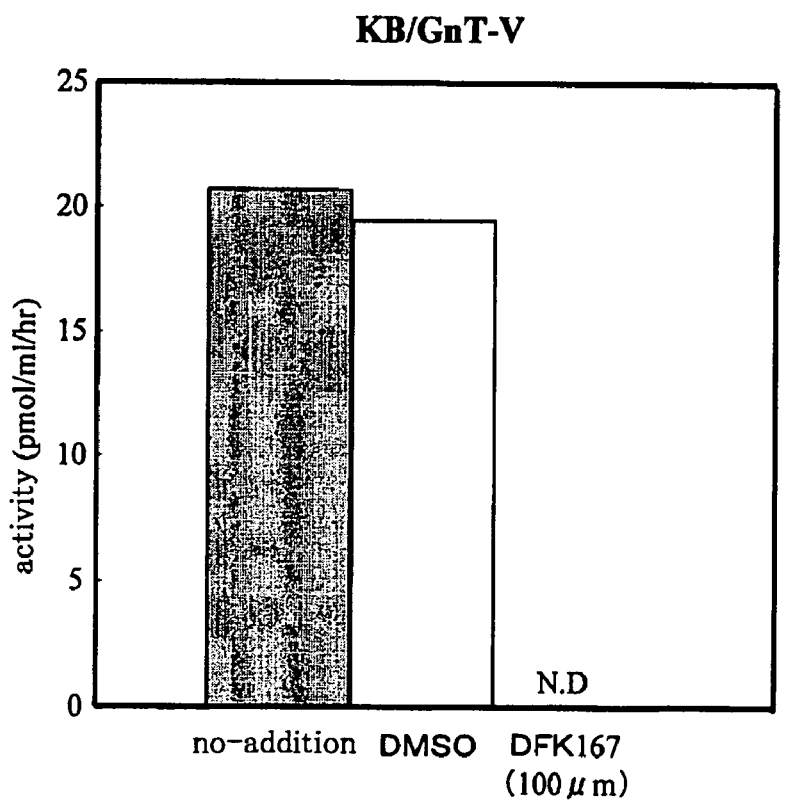

An influence of DFK167 (J. Med. Chem., 41, 6-9 (1998) known as an inhibitor for γ-secretase on production of secretory type GnT-V was examined. DFK167 was a compound represented by the above-mentioned formula (1) and available from ICN (Ohio, U.S.). A GnT-V gene was introduced into a pancreas cell MIA PaCa-2 and oral cavity cancer cell KB, and GnT-V was highly expressed to obtain cells which were cultured according to the method shown in Example 1, and then the activity of GnT-V in the culture solution was measured. The GnT-V activity in the culture solution of PaCa-2/GnT-V cells to which DMSO (dimethyl sulfoxide) had been added slightly decreased. As shown in FIGS. 10A and 10B, the GnT-V activity could not be detected in the culture solution of PaCa-2/GnT-V cell and KB/GnT-V cell to which DFK167 dissolved in DMSO had been added at a concentration of 100 μM. This indicates that cutting of GnT-V and secretion of secretory type GnT-V were inhibited completely by DFK167 which is a γ-secretase inhibitor. Therefore, it indicates that the γ-secretase inhibitor such as DFK 167 is a neovascularization inhibitor as one of the present inventions, and that the screening method using a cell in which GnT-V has been highly expressed shown in the above-mentioned examples also can be conducted as the method of screening a neovascularization inhibitor as one of the present inventions.

INDUSTRIAL APPLICABILITY

The present invention provides a peptide or protein having a neovascularization action, and a neovascularization accelerator containing this. This neovascularization accelerator is effective for wound healing or, for prevention and/or treatment of diseases related to arteriosclerosis, thrombosis, aneurysm, vascular obstruction.

Further, the present invention can suppress a neovascularization action by suppressing conversion of mature type GnT-V penetrating a membrane into secretory type GnT-V. A neovascularization action can be suppressed also by suppressing expression of GnT-V and suppressing binding of secretory type GnT-V to heparan sulfate proteoglycan. Such substances suppressing a neovascularization action are effective for prevention and/or treatment of diseases caused by neovascularization, typically including cancer metastasis and the like.

Furthermore, by use of an antibody to the above-mentioned peptide or protein containing a basic amino acid cluster region of GnT-V, the presence or absence or the amount of the above-mentioned peptide or protein in a test substance can be measured, and for example, a possibility of cancer metastasis can be found.

The invention claimed is:

1. An isolated polypeptide fragment of an N-acetylglucosaminyltransferase V (GnT-V), comprising a basic amino acid cluster region,
wherein the basic amino acid cluster region comprises the amino acid sequence of SEQ ID NO: 7 and up to 50 contiguous amino acids encoded by the sequence shown in SEQ ID NO: 6, or a variant thereof,
wherein the polypeptide fragment or variant thereof possesses neovascularization activity,
wherein the number of amino acids modified by addition, removal, or substitution in the variant is up to 10% of the number of amino acids in the basic amino acid cluster region, and
wherein the addition, removal, or substitution is conducted on amino acids other than basic amino acids.

2. The polypeptide of claim 1, wherein one amino acid other than a basic amino acid of the variant is added, removed, or substituted from the amino acid sequence encoded by the sequence shown in SEQ ID NO: 6.

3. The polypeptide of claim 1, wherein the number of basic amino acids accounts for greater than 30% of the total number of amino acids in said fragment.

4. The polypeptide of claim 1, consisting of the amino acid sequence shown in SEQ ID NO: 7.

5. A pharmaceutical composition comprising an amount of an isolated polypeptide consisting of SEQ ID NO: 7 sufficient to accelerate neovascularization.

6. A pharmaceutical composition comprising an amount of the polypeptide fragment of claim 1 sufficient to accelerate neovascularization, and a pharmaceutically acceptable carrier.

7. A pharmaceutical composition comprising an amount of the polypeptide fragment of claim 1 sufficient to promote wound healing and a pharmaceutically acceptable carrier.

8. A method for accelerating neovascularization comprising administering an amount of the polypeptide fragment of claim 1 sufficient to accelerate neovascularization and a pharmaceutically acceptable carrier therefor to a mammal.

9. A pharmaceutical composition comprising an amount of the polypeptide fragment of claim 1 sufficient to treat arteriosclerosis and a pharmaceutically acceptable carrier therefor.

* * * * *